United States Patent [19]

Keppel et al.

[11] 4,409,127

[45] Oct. 11, 1983

[54] ATTRITION RESISTANT METAL/OXYGEN COMPOSITIONS AND A PROCESS FOR THEIR PREPARATION

[75] Inventors: Robert A. Keppel, Seabrook, Tex.; Samuel J. Tremont, Manchester, Mo.; Emerson H. Lee; George D. Davis, both of Creve Coeur, Mo.

[73] Assignee: Monsanto Company, St. Louis, Mo.

[21] Appl. No.: 335,785

[22] Filed: Dec. 30, 1981

[51] Int. Cl.³ .................... B01J 21/04; B01J 23/14; B01J 23/18; B01J 23/84
[52] U.S. Cl. .................... 502/205; 502/336; 502/354; 502/355
[58] Field of Search .................... 252/463, 464, 466 J, 252/432

[56] References Cited

U.S. PATENT DOCUMENTS

| | | | |
|---|---|---|---|
| 3,668,151 | 6/1972 | Walker | 252/463 X |
| 3,925,447 | 12/1975 | Gelbein | 252/464 X |
| 3,957,691 | 5/1976 | Adachi et al. | 252/466 J |
| 4,260,845 | 4/1981 | Shioyama | 585/640 |

OTHER PUBLICATIONS

Above References A–B were cited by Applicants.

*Primary Examiner*—W. J. Shine

[57] ABSTRACT

Attrition resistant metal/oxygen compositions comprising the infusion and reaction product of alumina and at least one metal oxide, or compound convertible by heat to such metal oxide, which metal oxide is susceptible of undergoing infusion and reaction with the alumina, are useful in a wide variety of metal oxide-catalyzed reactions. The compositions are especially useful in reactions which involve reaction conditions of high stress, for example, vapor phase oxidations under fluidized bed conditions.

41 Claims, No Drawings

ATTRITION RESISTANT METAL/OXYGEN COMPOSITIONS AND A PROCESS FOR THEIR PREPARATION

CROSS-REFERENCE TO RELATED APPLICATIONS

"Attrition Resistant Metal/Oxygen Compositions," Ser. No. 335,791 and 335,792 and "Attrition Resistant Bismuth-Containing Metal/Oxygen Compositions," Ser. No. 335,786, all filed Dec. 30, 1981.

BACKGROUND OF THE INVENTION

1. Field of the Invention

This invention relates to attrition resistant metal/oxygen compositions and a process for preparing such compositions. More particularly, this invention relates to metal/oxygen compositions comprising the infusion and reaction product of:

(a) an alumina existing in a crystal form selected from the group consisting of $\gamma$, $\delta$, $\eta$, and $\chi$ crystal forms, and mixtures thereof, or that can be transformed by heat to such crystal forms, and characterized by
 (i) a mean particle size from about 10 $\mu$m to about 200 $\mu$m,
 (ii) a fractional porosity of at least 0.2,
 (iii) a surface area of at least 150 $m^2/g$, and
 (iv) a pore diameter such that at least 10 percent of the pores are less than 55 Å, and (b) at least one metal oxide, or compound convertible by heat to such metal oxide, having a maximum mean particle size of about 100 $\mu$m, with the proviso that the alumina/metal oxide mean particle size ratio is at least 2, which metal oxide is susceptible of undergoing infusion and reaction with the alumina upon being subjected to temperatures of at least 0.4 $T_m$ for a time sufficient to cause infusion and reaction between the metal oxide and the alumina, wherein $T_m$ is the melting point in °K. of the alumina.

The attrition resistant metal/oxygen compositions of this invention may be used for any of a wide variety of purposes generally known in the art. Thus, for example, the compositions are useful in the transformation of numerous organic compounds in the vapor phase such as dehydrogenation reactions, oxidation reactions, hydrogenation reactions, isomerization reactions, dealkylation reactions, dehydrocoupling reactions, and the like. The compositions may be employed in a manner identical to that for metal/oxygen compositions heretofore known in the art for such transformations.

2. Description of the Prior Art

Supported metal oxides are well-known as catalysts and oxygen carriers for a wide variety of chemical reactions. In general, such metal oxide compositions are comprised of a metal oxide coated on a support material of low porosity and low surface area. Such support is commonly referred to as an inert support. The method generally employed to produce these supported metal oxide compositions involves impregnating the inert support with a solution of a soluble salt of the metal oxide, separating the resultant impregnated solid, and heating to remove a substantial portion of the solvent. The impregnated solid is then calcined at elevated temperatures to convert the metal salt to the corresponding metal oxide. Multiple impregnations are sometimes employed to achieve an increased concentration of metal oxide on the support.

Another well-known technique employed for forming supported metal oxide compositions involves suspending the support materials in a solution of a salt of the metal, completely or partially evaporating the solvent, and possibly mixing the resultant material with an organic binder and pelletizing thereof. The dry pellet is then heated to an elevated temperature to effect complete dehydration and burning out of the organic material.

A method for forming a supported metal oxide on a porous support is disclosed in U.S. Pat. No. 3,925,447 which involves contacting the porous support material with the metal oxide in molten form to produce a catalyst in which the metal oxide is substantially entirely within the pores of the support. The resultant catalyst is used in the production of nitriles.

U.S. Pat. No. 3,668,151 discloses a high strength (as indicated by its crush strength) zinc aluminate catalyst composition. Upon being impregnated with platinum, lithium, and tin in the usual manner, the resultant catalyst was used to dehydrogenate n-butane to olefins and diolefins, presumably 1- and 2-butene and 1,3-butadiene.

A substantially identical zinc aluminate catalyst having an approximate mole ratio of zinc oxide to alumina of 1 also is disclosed in U.S. Pat. No. 4,260,845. The catalyst is reported to be useful for dehydration of saturated alcohols to olefins, for example, 2-methyl-1-butanol to 2-methyl-1-butene.

Although these prior art compositions are generally suitable for their stated purposes, the commercial utility of catalysts and oxygen carrier compositions in reactions which involve reaction conditions of high stress (such as high temperatures and/or pressures, especially under fluidized bed conditions) require compositions which are highly resistant to abrasion and attrition due to the deleterious effects of reaction conditions. Accordingly, research efforts are continually being made for high efficiency catalyst and oxygen carrier compositions of increased physical strength and attrition resistance which are useful in reactions involving conditions of high stress. The discovery of the compositions of the present invention, therefore, is believed to be a decided advance in the catalyst and oxygen carrier composition art.

SUMMARY OF THE INVENTION

It is an object of this invention to provide attrition resistant metal/oxygen compositions.

Another object of this invention is to provide attrition resistant metal/oxygen compositions highly effective for the vapor phase transformation of organic compounds.

Yet another object of this invention is to provide attrition resistant metal/oxygen compositions highly effective as combination catalyst/oxygen carrier compositions in the vapor phase oxidative dehydrocoupling of toluene to yield toluene dehydrocoupled products in high yields and selectivities.

Still another object of this invention is to provide a process for the preparation of attrition resistant metal/oxygen compositions effective for the vapor phase transformation of organic compounds.

To achieve these and other objects which will become apparent from the accompanying description and claims, attrition resistant metal/oxygen compositions are provided which comprise the infusion and reaction product of:
 (a) an alumina existing in a crystal form selected from the group consisting of $\gamma$, $\delta$, $\eta$, and $\chi$ crystal forms, and mixtures thereof, or that can be transformed by heat to such crystal forms, and characterized by
  (i) a mean particle size from about 10 $\mu$m to about 200 $\mu$m,
  (ii) a fractional porosity of at least 0.2,
  (iii) a surface area of at least 150 m$^2$/g, and
  (iv) a pore diameter such that at least 10 percent of the pores are less than 55 Å, and
 (b) at least one metal oxide, or compound convertible by heat to such metal oxide, having a maximum mean particle size of about 100 $\mu$m, with the proviso that the alumina/metal oxide mean particle size ratio is at least 2, which metal oxide is susceptible of undergoing infusion and reaction with the alumina upon being subjected to temperatures of at least 0.4 $T_m$ for a time sufficient to cause infusion and reaction between the metal oxide and the alumina, wherein $T_m$ is the melting point in °K. of the alumina.

The provision of the process for the preparation of such compositions object is achieved by a process which comprises:
 (a) forming a mixture of an alumina existing in a crystal form selected from the group consisting of $\gamma$, $\delta$, $\eta$, and $\chi$ crystal forms, and mixtures thereof, or that can be transformed by heat to such crystal forms, and characterized by
  (i) a mean particle size from about 10 $\mu$m to about 200 $\mu$m,
  (ii) a fractional porosity of at least 0.2,
  (iii) a surface area of at least 150 m$^2$/g, and
  (iv) a pore diameter such that at least 10 percent of the pores are less than 55 Å, and at least one metal oxide, or compound convertible by heat to such metal oxide, having a maximum mean particle size of about 100 $\mu$m, with the proviso that the alumina/metal oxide mean particle size ratio is at least 2, which metal oxide is susceptible of undergoing infusion and reaction with the alumina, and
 (b) heating the mixture to a temperature of at least 0.4 $T_m$ for a time sufficient to cause infusion and reaction between the metal oxide and the alumina, wherein $T_m$ is the melting point in °K. of the alumina.

The provision of the toluene dehydrocoupling process object is achieved by a process which comprises:
 (a) contacting the toluene in the vapor phase at a temperature from about 450° C. to about 650° C. with an attrition resistant metal/oxygen composition comprising the infusion and reaction product of
  (i) an alumina existing in a crystal form selected from the group consisting of $\gamma$, $\delta$, $\eta$, and $\chi$ crystal forms, and mixtures thereof, or that can be transformed by heat to such crystal forms, and characterized by
   (a) a mean particle size from about 10 $\mu$m to about 200 $\mu$m,
   (b) a fractional porosity of at least 0.2,
   (c) a surface area of at least 150 m$^2$/g, and
   (d) a pore diameter such that at least 10 percent of the pores are less than 55 Å, and
  (ii) at least one metal oxide, or compound convertible by heat to such metal oxide, having a maximum mean particle size of about 100 $\mu$m, with the proviso that the alumina/metal oxide mean particle size ratio is at least 2, which metal oxide is susceptible of undergoing infusion and reaction with the alumina upon being subjected to temperatures of at least 0.4 $T_m$ for a time sufficient to cause infusion and reaction between the metal oxide and the alumina, wherein $T_m$ is the melting point in °K. of the alumina, and
 (b) recovering the toluene dehydrocoupled product.

Other objects and advantages of the present invention will become apparent from the accompanying description and claims.

DESCRIPTION OF THE PREFERRED EMBODIMENTS

1. The Compositions

The attrition resistant metal/oxygen compositions of the present invention comprise the infusion and reaction product of:
 (a) an alumina existing in a crystal form selected from the group consisting of $\gamma$, $\delta$, $\eta$, and $\chi$ crystal forms, and mixtures thereof, or that can be transformed by heat to such crystal forms, and characterized by
  (i) a mean particle size from about 10 $\mu$m to about 200 $\mu$m,
  (ii) a fractional porosity of at least 0.2,
  (iii) a surface area of at least 150 m$^2$/g, and
  (iv) a pore diameter such that at least 10 percent of the pores are less than 55 Å, and a maximum mean particle size of about 100 $\mu$m, with the proviso that the alumina/metal oxide mean particle size ratio is at least 2, which metal oxide is susceptible of undergoing infusion and reaction with the alumina upon being subjected to temperatures of at least 0.4 $T_m$ for a time sufficient to cause infusion and reaction between the metal oxide and the alumina, wherein $T_m$ is the melting point in °K. of the alumina.

The attrition resistant characteristics of the metal/oxygen compositions of the present invention, preferably an attrition rate less than 0.5 weight percent/hour (as measured by an accelerated attrition test described below), make them excellent for use in reactions which involve reaction conditions of high stress, particularly in a fluidized bed system at elevated temperatures and/or pressures.

The term "infusion" and related terms are employed herein to mean a process by which two adjacent solids of differing compositions homogenize by diffusion of one of such solids into the other, for example, the diffusion of the metal oxide into the alumina.

The term "fractional porosity" is employed herein to mean the ratio of void space or volume in a particle to the bulk or total volume of that particle.

The term "attrition," as employed herein, means the art of wearing or grinding down by friction and breakage of the structures into dust and fines.

The term "attrition rate," as employed herein, means an accelerated attrition rate and refers to the rate of attrition as determined by an accelerated attrition test described in Example 44, below.

The materials suitable for use as components of the metal/oxygen compositions of this invention must, of necessity, possess those properties and characteristics which will yield attrition resistant compositions. In addition, the component materials advantageously should yield metal/oxygen compositions which are suitably for the vapor phase transformation of organic compounds, especially the dehydrocoupling of toluene, to yield the desired products in high yields and selectivities. Such materials are available commercially from numerous catalyst and metal oxide suppliers.

Aluminas which are useful as components of the attrition resistant metal/oxygen compositions are fairly wide in scope. Such aluminas, however, must possess certain characterizing properties to be suitable for use in the present invention. Included among such properties are (a) a mean particle size from about 10 $\mu$m to about 200 $\mu$m, and preferably from about 20 $\mu$m to about 125 $\mu$m; and (b) a fractional porosity of at least 0.2, with values from about 0.2 to about 0.8 being preferred, a surface area of at least 150 m$^2$/g, and a pore diameter such that at least 10 percent, preferably 30 percent, of the pores are less than 55 Å (5.5 mm). In order to facilitate ease of fluidization, the alumina particles preferably are spheroidal in shape.

Aluminas suitable for use in the present invention are those which possess the aforementioned characterizing properties and, in addition, exist predominantly in a crystal form selected from the group consisting of gamma ($\gamma$), delta ($\delta$), eta ($\eta$), and chi ($\chi$) crystal forms, and mixtures thereof, or that can be transformed by heat to these crystal forms. Included among the latter grouping are hydrated aluminas such as Boehmite, pseudo-Boehmite, Bayerite, and Gibbsite.

Metal oxides suitable for use within the scope of the present invention are not narrowly critical. Each metal oxide must, of necessity, be susceptible of undergoing infusion and reaction with the alumina under conditions hereinafter described to yield the attrition resistant metal/oxygen composition. In addition, the metal oxide must have a maximum mean particle size of about 100 $\mu$m, with the proviso that the alumina/metal oxide mean particle size ratio is at least 2, and preferably 15 or more. The stated mean particle size ratio permits the metal oxide and the alumina to undergo the desired infusion and reaction with little, if any, material change in the original particle size of the alumina. This phenomenon results in the high strength attrition resistant metal/oxygen compositions of this invention.

Suitable metal oxides are exemplified by oxides of lithium (Li$_2$O), sodium (Na$_2$O), potassium (K$_2$O), rubidium (Rb$_2$O), cesium (Cs$_2$O) of Group 1a; beryllium (BeO), magnesium (MgO), calcium (CaO), strontium (SrO), barium (BaO) of Group 2a; scandium (Sc$_2$O$_3$), and yttrium (Y$_2$O$_3$) of Group 3b; zirconium (ZrO$_2$) of Group 4b; vanadium V (V$_2$O$_5$) of Group 5b; zinc (ZnO) and cadmium (CdO) of Group 2b; boron (B$_2$O$_3$), gallium (Ga$_2$O$_3$), indium (In$_2$O$_3$), and thallium (Tl$_2$O$_3$) of Group 3a; germanium IV (GeO$_2$), tin IV (SnO$_2$), and lead II (PbO) of Group 4a; phosphorus, arsenic, antimony, and bismuth of Group 5a; lanthanides; actinides; Groups 1b, 6b, 7b, and 8 of the Periodic Table of the Elements, and mixtures thereof.

Of these metal oxides, the oxides of potassium, calcium, zirconium, iron, boron, lead, antimony, and bismuth, and mixtures thereof are preferred, especially for toluene dehydrocoupling reactions.

It will be noted, however, that while metal oxides are preferred for use in the present invention, the direct charging of metal oxides as starting materials is not necessary. Any compound of the desired metal such as salts, hydroxides, and the like, which are convertible by heat to the corresponding metal oxide, and as such, may be considered as a precursor thereof, may be used to provide indirectly the metal oxide for preparing the attrition resistant metal/oxygen compositions of the present invention. Typical metal salts include the water-soluble nitrates, carbonates, and acetates.

The term "Periodic Table of the Elements" as employed herein refers to the Periodic Table of the Elements published in CRC Handbook of Chemistry and Physics, 60th ed., Weast, Ed., CRC Press Inc., Boca Raton, Fla. 1979, Inside Front Cover.

The metal oxide component ranges in an amount from about 20 mole percent to about 65 mole percent, based on the total number of moles of metal oxide and alumina in the metal/oxygen composition, and preferably from about 30 mole percent to about 55 mole percent. The alumina component makes up the remaining portion of the metal/oxygen composition, which, in view of the stated mole percent of the metal oxide component, must range from about 35 mole percent to about 80 mole percent. Preferably, however, the alumina component constitutes from about 45 mole percent to about 70 mole percent of the metal/oxygen composition.

Alumina concentrations greater and less than the stated 35 to 80 mole percent range, surprisingly, have been found to be detrimental. Compositions having alumina concentrations outside the stated range (35 to 80 mole percent) exhibit a marked decrease in attrition resistance or, stated differently, an increase in attrition rae. Lowered attrition resistance, of course, results in increased abrasion, breakage, and dusting of composition structures under high stress use conditions. Such abrasion, breakage, and dusting can cause undesirable pressure drop, flow problems, filter clogging, loss of fluidizability, and the like under such conditions, especially during operations employing fluidized bed reactor systems.

The attrition resistant metal/oxygen compositions can be prepared in several ways. The simplest method involves intimately mixing at least one suitable metal oxide having a maximum mean particle size of about 100 $\mu$m with the desired alumina having a mean particle size from about 10 $\mu$m to about 200 $\mu$m such that the alumina/metal oxide mean particle size ratio is at least 2, in an amount sufficient to constitute from about 20 mole percent to about 65 mole percent of the composition. The metal oxide and alumina components may be dry mixed or mixed by slurrying in a suitable wetting agent (wet mixed), for example, water or an organic compound such as methanol, ethanol, and the like. When a wetting agent is employed in the mixing step, it is removed by heating the slurried mixture at a temperature and for a time sufficient to substantially remove the excess wetting agent. In general, heating at a temperature of about 150° C. to about 250° C., usually about 200° C., for about 1 hour to about 5 hours, usually 2 hours, is sufficient. It will be recognized, however, that the actual time and temperature will depend upon the particular wetting agent employed, the quantity of material, and the like. The dry mixed material may also be subjected to similar temperatures in order to remove any physically bound water. Continued heating of the dry mixture (from either the wet-mixed or dry-mixed components) at temperatures from about 250° C. to about 500° C. for about 1 hour to about 5 hours serves to decompose any salts which are present and remove other volatile components.

Upon completion of the drying and removal of any other volatile components, the dry mixture of metal oxide and alumina is calcined at a temperature of at least 0.4 $T_m$ for a time sufficient to cause the metal oxide and the alumina to infuse in accordance with diffusional behavior in metal oxides as described in Freer, *Journal of Material Science*, 15, 803–824 (1980) and undergo reaction to yield the attrition resistant metal/oxygen compositions of the present invention. The calcination may be carried out in an inert atmosphere such as nitrogen, helium, and the like, or in air. In many instances, it may be desirable to conduct the initial calcination under an inert atmosphere in order to prevent oxidation of the metal ion of the metal oxide to a higher oxidation state which may prevent or severely curtail the necessary infusion. This initial calcination is then followed by a final calcination in air to form the desired metal/oxygen composition.

As previously noted, the calcination is carried out by heating the dry mixture of metal oxide and alumina to a temperature of at least 0.4 $T_m$. It will be recognized that the actual temperature employed will depend primarily on the diffusional behavior of the metal oxide with the particular alumina. In a similar manner, the actual time employed will depend upon the component materials employed, as well as the calcination temperature. As an example, since alumina has a melting point of about 2273° K. (2000° C.), temperatures typically from about 800° C. (0.47 $T_m$) to about 1400° C. (0.74 $T_m$) and a time from about 1 hour to about 15 hours are sufficient. Preferably, a temperature from about 900° C. to about 1100° C. and a time from about 8 hours to about 12 hours are employed, most preferably, a temperature from about 1000° C. to about 1050° C. and a time from about 10 hours to about 11 hours.

The calcination (and infusion) may be effected in any calcination apparatus known to the art. Non-limiting examples include ovens or muffle furnaces containing fixed beds or moving beds, rotary kilns, and the like.

In an alternative method of preparation, a suitable precursor hydroxide or salt of the metal oxide component such as a nitrate, carbonate, or acetate is intimately mixed with the alumina and infused and calcined as previously described. Another method involves the impregnation of the alumina with an aqueous solution of one or more of the precursor salts. Preferably, a high concentration of metal salt is employed in order to minimize the need for subsequent evaporation of solvent. After the impregnation, the resultant product is subjected to the infusion and calcining process as previously described.

2. Characterization of the Compositions

The attrition resistant metal/oxygen compositions of this invention are substantially free of unreacted metal oxide and alumina as determined by x-ray diffraction (XRD). That is, the starting material components, under the heating and/or calcining conditions employed, have undergone infusion and reaction to an extent sufficient to preclude having the starting material components remain in an unreacted state. As a result, the compositions of the present invention are not simply active materials supported on a porous support material; they, instead, are novel compositions comprising the infusion and reaction product of an alumina and at least one metal oxide, all as previously defined.

The compositions of this invention exhibit excellent attrition resistance when compared to supported catalysts and compositions of the prior art. An attrition rate less than 0.5 weight percent/hour is, in general, preferred. In addition, the compositions demonstrate high activities, as well as high selectivities, in the many and varied transformations of organic compounds. In a preferred use embodiment, compositions prepared from oxides of lead, antimony, or bismuth, and mixtures thereof, and the previously described alumina have been found to be particularly efficacious as oxygen carriers and/or catalysts in the dehydrocoupling of toluene to stilbene and/or bibenzyl. Overall, and in general, metal and metal ions employed as catalysts in known prior art processes may be employed in the metal/oxygen compositions of this invention in the same mode to effect similar reactions, but with the added advantage of increased attrition resistance.

The attrition resistance, calculated as the attrition rate in units of weight percent/hour is determined by an accelerated attrition test. In this test, which is described in detail in Example 44 below, the weight in grams of dust and fines generated via abrasion, friction, and breakage under stated conditions for a specified period of time, usually the 5–21 hour period (16 hours) out of a total of 21 hours, from a specified weight in grams of a sample of the bulk composition is measured. Using these values, the percent attrition during the specified period can be calculated as follows:

$$\% \text{ Attrition} = \frac{\text{Dust and Fines (5-21 Hour Period), g}}{\text{Initial Weight, g} - \text{Dust and Fines (0-5 Hr. Period), g}} \times 100$$

The attrition rate is then calculated as follows:

$$\text{Attrition Rate} = \frac{\% \text{ Attrition}}{\text{Time Period, Hours}}$$

It will be apparent, of course, that all things being equal with respect to properties exhibited by the metal/oxygen compositions of this invention, the greater the attrition resistance (expressed as a smaller numerical attrition rate value in units of weight percent/hour), the more desirable such compositions become in that fewer difficulties associated with high rates of attrition (lack of attrition resistance) are experienced during use in reactions involving conditions of high stress. An attrition rate less than 0.5 weight percent/hour, as previously noted, for the compositions of this invention is preferred, with values of 0.3 weight percent/hour or less being most preferred.

The specific surface area value desirable for a given metal/oxygen composition depends primarily on its intended use. As an example, compositions useful in the dehydrocoupling of toluene preferably will exhibit surface area values less than 5 $m^2/g$, with values from about 0.05 $m^2/g$ and 1 $m^2/g$ being most preferred. Such values result in greater activities and selectivities to the toluene dehydrocoupled products. Conversely, higher surface area compositions, especially those having surface areas greater than 5 $m^2/g$, exhibit decreased selectivities to the toluene dehydrocoupled products as evidenced by the undesirable tendency toward increased benzene and carbon dioxide production during such dehydrocoupling reactions.

The surface area of the metal/oxygen compositions of this invention is measured according to the BET method [from Brunauer et al, *Journal of the American*

Chemical Society, 60, 309–319 (1938)] described in ASTM D 3663-78 using a Micromeritics Digisorb 2500 instrument. In general, however, for samples having a relatively low surface area, for example, less than 5 m²/g, krypton is preferably substituted for nitrogen as the adsorption gas for increased accuracy of measurement. Examples of metal/oxygen compositions of the invention may be represented by the empirical formulas $Pb_{10}Sb_3Bi_2O_x(Al_2O_3)_{7-28}$ and $Bi_{15-30}K_{4-5}Zr_{1-2}O_x(Al_2O_3)_{16-29}$, wherein x is a number taken to satisfy the average valences of the metal in the oxidation states in which they exist in the composition.

3. Transformation of Organic Compounds

The attrition resistant metal/oxygen compositions of this invention, as previously noted, are useful for the transformation of organic compounds in the vapor phase. For convenience and clarity, however, the use of the metal/oxygen compositions will be described with reference to a process to oxidatively dehydrocouple toluene to produce toluene dehydrocoupled products, namely, stilbene and bibenzyl. As noted previously, such compositions preferably exhibit an attrition rate less than 0.5 weight percent/hour and, for use in the toluene dehydrocoupling process herein described, a surface area less than 5 m²/g.

The attrition resistant metal/oxygen compositions of this invention function in a catalytic mode, a stoichiometric mode as an oxidant or oxygen carrier, or a combined catalytic/stoichiometric mode for the dehydrocoupling of toluene.

In the catalytic mode of operation, oxygen or an oxygen-containing gas such as air or oxygen-enriched air is reacted with toluene in the presence of the attrition resistant metal/oxygen composition in an amount sufficient for the dehydrocoupling reaction. In the stoichiometric mode of operation, the attrition resistant metal/oxygen composition is the sole source of oxygen. That is, in the latter instance the dehydrocoupling of toluene is conducted in the substantial absence of added free oxygen such as would be obtained from air. In the combined catalytic/stoichiometric mode of operation, oxygen or an oxygen-containing gas is added as a reactant in a manner similar to that noted previously for the catalytic mode of operation. However, the amount of added oxygen is not sufficient for the dehydrocoupling reaction and the required additional oxygen must be supplied by the attrition resistant metal/oxygen composition.

Of these three modes of operation, the stoichiometric mode is generally preferred in that undesirable side reactions—oxidative dealkylation, for example, to product benzene and carbon dioxide—are substantially reduced. It will, of course, be recognized that in spite of the undesirability of producing benzene during the course of the toluene dehydrocoupling reaction, benzene is a valuable article of commerce. It is therefore highly desirable to recover the benzene values when substantial production thereof occurs. The recovery and purification of such benzene values may be accomplished by any standard method and means known to the art.

The term "dehydrocoupling" and related terms are employed herein to mean the toluene molecules are coupled or dimerized—with carbon-carbon bond formation occurring between the methyl group carbons—and the coupled molecules have lost either one or two hydrogen atoms from the methyl group of each toluene molecule. When two hydrogen atoms per molecule of toluene are lost, the carbon-carbon bond at the coupling or dimerization site is unsaturated as by dehydrogenation. That is, stilbene is the product. On the other hand, bibenzyl, having a saturated carbon-carbon bond at the coupling site, is the product when only one hydrogen atom per molecule of toluene is lost.

In general, the production of stilbene as the toluene dehydrocoupled product is preferred over the production of bibenzyl. This stated preference is due to the unsaturated character of stilbene as opposed to the saturated character of bibenzyl. And, as is well known in the art, the presence of the unsaturated olefinic carbon-carbon double bond causes the stilbene to exhibit high reactivity, thereby facilitating its direct use as an organic intermediate in numerous organic syntheses.

The toluene dehydrocoupling process using the attrition resistant metal/oxygen compositions of this invention is conveniently carried out in an apparatus of the type suitable for carrying out chemical reactions in the vapor phase. It can be conducted in a single reactor or in multiple reactors using either a fixed bed, a moving bed, or a fluidized bed system to effect contacting of the reactant or reactants and the attrition resistant metal/oxygen composition. In general, a fluidized bed system is preferred in that it advantageously possesses the ability to approach isothermal conditions during the course of the reaction process. Moreover, the attrition resistant metal/oxygen compositions of this invention are particularly suited for use in a fluidized bed system due to the low attrition rate and small particle size (mean particle size from about 10 μm to about 200 μm). It would be apparent, of course, that when using a fluidized bed system, fluid velocities (linear gas velocities) must be sufficient to maintain a uniform suspension of the particles of the attrition resistant metal/oxygen composition, but insufficient to sweep the particles out of the reactor. Gas velocities in the range between about 1.52 cm/sec (0.05 ft/sec) to about 91.44 cm/sec (3.0 ft/sec) are usually sufficient, depending on factors such as the relative densities of the gas and solid, gas viscosity, the size and shape of the solid particles, the number of particles per unit volume (bed density), the size and configuration of the reactor, and the like.

Regardless of the particular type of reactor employed—whether fixed bed, moving bed, or a fluidized bed system—the reactant toluene will generally be heated and introduced to the reactor as a vapor. However, the reactant may be introduced to the reactor as a liquid and then vaporized.

The oxidative dehydrocoupling reaction is carried out in the vapor phase and under the influence of heat. The temperature range under which the reaction can be carried out ranges from about 450° C. to about 650° C. and preferably is conducted at from about 500° C. to about 600° C., most preferably at about 575° C.

Pressure is not critical in the toluene dehydrocoupling process of this invention. The reaction may be carried out at subatmospheric, atmospheric, or superatmospheric pressures as desired. It will be generally preferred, however, to conduct the reaction at or near atmospheric pressure. Generally, pressures from about $2.53 \times 10^4$ pascals or Pa (0.25 atmosphere or atm) to about $4.05 \times 10^5$ Pa (4.0 atm) may be conveniently employed.

The reaction time for the contact of the reactants with the attrition resistant metal/oxygen compositions of this invention may be selected from a broad operable range which may vary from about 0.1 to about 60 seconds. The reaction time may be defined as the length of time in seconds which the reactant gases measured under reaction conditions are in contact with the attrition resistant metal/oxygen composition in the reactor. The reaction time may vary depending upon the reaction temperature and the desired toluene conversion level. At higher temperatures and lower toluene conversion levels, shorter contact times are required. Generally, the contact time will vary from about 0.5 seconds to about 20 seconds. Preferably, for optimum conversion and selectivity in the preferred temperature range, a contact time from about 1 second to about 12 seconds is employed.

In addition to the toluene, other inert substances such as nitrogen, helium, and the like may be present in the reactor. Such inert materials may be introduced to the process alone or may be combined with the other materials as feed. Water or steam may be added to the reaction zone, preferably being introduced with the feed in order to improve the selectivity to the desired product(s) and particularly to suppress complete oxidation to $CO_2$. Steam/hydrocarbon mole ratios in the range from about 0.1 to about 10 or more are suitable, the upper limit being determined by practical cost considerations. Mole ratios in the range from about 0.5 to about 3 are preferred.

The attrition resistant metal/oxygen compositions of this invention contain oxygen in such a manner that they are capable of releasing stoichiometric quantities of oxygen under the oxidative reaction conditions employed to dehydrocouple toluene as described hereinbelow. The oxygen in the compositions is associated with the metals as oxides, as oxygen complexes, or as mixtures of oxides and complexes.

As previously noted, the dehydrocoupling reaction may be conducted in the presence or absence of added free oxygen. When oxygen is not added to the system, that is, the reaction is conducted in the stoichiometric mode of operation, the oxygen required for the reaction is provided by the metal/oxygen composition which enters into the reaction and is consequently reduced (or, in actual practice, partially reduced) during the course of the reaction. This necessitates regeneration or reoxidation which can be easily effected by heating the material in air or oxygen at temperatures from about 500° C. to about 650° C. for a period of time ranging from about 5 seconds to about 1 hour. In a semicontinuous operation, regeneration can be effected by periodic interruption of the reaction for reoxidation of the reduced composition, that is, periods of reaction are cycled with periods of regeneration. Operation, however, can be on a continuous basis whereby a portion of the attrition resistant metal/oxygen composition can be continuously or intermittently removed, reoxidized, and the reoxidized material can thereafter be continuously or intermittently returned to the reaction. The latter method is particularly adapted to operations in which the attrition resistant metal/oxygen composition is employed in the form of a moving bed or the preferred fluidized bed.

When oxygen is employed as a reactant, the reaction may be conducted in either a catalytic mode of operation or a combined catalytic/stoichiometric mode of operation, depending on the amount of oxygen supplied. In the catalytic mode of operation, oxygen is supplied in an amount sufficient for the dehydrocoupling reaction. The actual amount of oxygen supplied may be specified as a function of the amount of the toluene. On this basis, the amount of oxygen supplied is ordinarily selected to provide a toluene/oxygen mole ratio from about 1 to about 8 and preferably from about 2 to about 6.

In the combined catalytic/stoichiometric mode of operation, the amount of oxygen supplied as a reactant is not sufficient for the dehydrocoupling reaction, thereby requiring an additional source of oxygen. The required additional oxygen will be supplied by the attrition resistant metal/oxygen composition, that is, the composition will serve as the additional source of oxygen. As a result, the attrition resistant metal/oxygen composition enters into the reaction and is consequently reduced during the course of the reaction. This necessitates regeneration or reoxidation of the reduced composition which can be easily effected as described previously for the stoichiometric mode of operation.

In either mode of operation employing added oxygen as a reactant, whether catalytic or combined catalytic/stoichiometric, the added free oxygen may be supplied either as oxygen or an oxygen-containing gas such as air or oxygen-enriched air.

As previously indicated, the toluene dehydrocoupling process employing the attrition resistant metal/oxygen compositions of this invention is preferably carried out in the absence of added free oxygen, that is, in the stoichiometric mode of operation, and utilizes only that oxygen supplied by the attrition resistant metal/oxygen composition. Also, with few exceptions, at substantially comparable conditions, the lower the toluene conversion level, the higher will be the selectivity to the dehydrocoupled products. That is, under similar conditions, the selectivity to the dehydrocoupled toluene product is in general inversely proportional to the toluene conversion level. However, for practical reasons, the dehydrocoupling reaction will generally be conducted at a toluene conversion level of about 20 to about 55 percent.

The toluene dehydrocoupled products, stilbene and bibenzyl, may be recovered and purified by an appropriate method and means known to the art and further elucidation here will be unnecessary duplication of the art. As noted previously, stilbene, of course, if the preferred product.

The following specific examples illustrating the best presently known methods of practicing the invention are described in detail in order to facilitate a clear understanding of the invention. It should be understood, however, that the detailed expositions of the application of the invention, while indicating preferred embodiments, are given by way of illustration only and are not to be construed as limiting the invention since various changes and modifications within the spirit of the invention will become apparent to those skilled in the art from this detailed description.

EXAMPLE 1

Alumina Preparation

The alumina was sieved for 30 minutes. The material less than 120 mesh (U.S. Standard Sieve Size; 125 μm) or 70 mesh (200 μm), as indicated, and larger than 400 mesh (38 μm), 325 mesh (45 μm), or 200 mesh (75 μm), as indicated, was retained. The retained material was sieved twice more on clean mesh screens of the previously indicated size. Each time the −20, +400 (120/400), −70, +325 (70/325), or −70, +200

(70/200) mesh material, as indicated, was retained. A sufficient quantity of the triply sieved alumina was accurately weighed for use in preparing the attrition resistant metal/oxygen compositions.

Properties of numerous representative aluminas (Al$_2$O$_3$) are tabulated in Table 1.

organic compounds, with the dehydrocoupling of toluene being used for illustrative purposes).

EXAMPLES 2-10

The following is a general procedure for the preparation of a metal/oxygen composition using a wetting

TABLE 1
REPRESENTATIVE ALUMINAS AND PROPERTIES[1]

| SAMPLE NO. | BRAND IDENTIFICATION | CRYSTAL PHASE[2] INITIAL | AFTER 2 HR @ 550° C. | WATER (CHEMICAL) Wt. %[3] | PARTICLE SIZE DISTRIBUTION, %[4] μm | | | | |
|---|---|---|---|---|---|---|---|---|---|
| | | | | | <20 | 20-45 | 45-88 | 88-125 | >125 |
| 1-A | Alcoa FAH (SF-30)[11] | Boehmite and Gibbsite | α and χ | 6.5 | 11 | 3 | 25 | 28 | 33 |
| 1-B | Calsicat 49B-048A[12] | δ and θ | δ and θ | 1.0 | 5 | 26 | 52 | 13 | 4 |
| 1-C | Catapal SB[13] | α and Boehmite | α and γ | 14.5 | 12 | 20 | 36 | 22 | 10 |
| 1-D | Harshaw 1465P[14] | γ | γ | 2.0 | 9 | 24 | 49 | 12 | 6 |
| 1-E | Harshaw 3970P[14] | γ | γ | 2.4 | 2 | 22 | 44 | 22 | 10 |
| 1-F | Kaiser A-300[15] | χ | χ | 5.0 | 12 | 24 | 30 | 24 | 10 |
| 1-G | Ketjen D[16] | Boehmite | γ | 14.5 | 12 | 33 | 50 | 4 | 1 |
| 1-H | Ketjen M[16] | Boehmite | γ | 14.5 | 8 | 15 | 43 | 21 | 13 |
| 1-I | Norton SA6373[17] | Boehmite | γ | 12.0 | 12 | 11 | 20 | 44 | 13 |
| 1-J | Norton 74368[17] | Boehmite | γ | 7.0 | 2 | 35 | 55 | 15 | 5 |
| 1-K | Norton 74380[17] | Boehmite | γ and χ | 8.1 | 11 | 28 | 52 | 7 | 2 |
| 1-L | Alcoa F-1-100[11] | γ and Boehmite | γ | 14.8 | 7.5 | 22.5 | 40 | 23.7 | 6.3 |

| SAMPLE NO. | BET SURFACE AREA, m²/g[5] | DENSITY, g/cc PARTICLE[6] | SKELETAL[7] | BULK[8] | POROSITY[9] FRACTIONAL[10] | % <55 Å[9] | MEAN PORE DIAMETER, Å[9] |
|---|---|---|---|---|---|---|---|
| 1-A | 151.5 | 1.78 | 3.27 | 1.23 | 0.455 | 76.1 | 37.5 |
| 1-B | 91.1 | 1.42 | 3.57 | 0.72 | 0.602 | 1.0 | 125.0 |
| 1-C | 226.0 | 1.15 | 3.48 | 0.99 | 0.670 | 16.3 | 67.5 |
| 1-D | 147.8 | 1.42 | 3.35 | 0.89 | 0.576 | 11.0 | 77.5 |
| 1-E | 196.5 | 1.18 | 3.56 | 0.86 | 0.669 | 14.5 | 72.5 |
| 1-F | 154.9 | 1.68 | 3.27 | 1.21 | 0.486 | 74.0 | 47.5 |
| 1-G | 257.4 | 1.04 | 3.29 | 0.90 | 0.684 | 44.0 | 57.5 |
| 1-H | 280.0 | 1.27 | 3.12 | 1.00 | 0.593 | 47.0 | 62.5 |
| 1-I | 235.0 | 1.38 | 3.65 | 0.94 | 0.622 | 42.1 | 57.5 |
| 1-J | 206.0 | 1.16 | 3.28 | 0.82 | 0.646 | 16.6 | 72.5 |
| 1-K | 186.0 | 1.60 | 3.075 | 0.80 | 0.480 | 80.0 | 57.5 |
| 1-L | 210.0 | 1.44 | 3.43 | 0.88 | 0.580 | 69.7 | 42.5 |

[1]Physical property measurements were performed on heat treated aluminas (after 2 hours at 550° C.).
[2]Analyses were performed using a Philips Diffractometer.
[3]Determined by heating an accurately weighed sample to constant weight and by differential thermal analysis (DTA).
[4]Measured according to the manufacturer's procedure using a Leeds & Northrup Microtrak instrument.
[5]Measured according to ASTM D 3663-78 for surface area of catalysts using a Micromeritics Digisorb 2500 instrument.
[6]Measured by mercury displacement using an Aminco-Winslow Porisimeter.
[7]Determined using a Micromeritics Helium Pycnometer.
[8]Determined by accurately weighing a given volume of compacted material.
[9]Determined by nitrogen desorption using a Micromeritics Digisorb 2500 instrument.
[10]Calculated using the mathematical relationship, $$F.P. = \frac{\rho_{He} - \rho_{Hg}}{\rho_{He}}$$

where F.P. is the fractional porosity, $\rho_{He}$ is the skeletal density, and $\rho_{He}$ is the particle density.
[11]Available commercially from Aluminum Company of America, 1501 Alcoa Bldg., Pittsburgh, PA 15219.
[12]Obtained from Mallinckrodt, Inc., Calsicat Div., 1707 Gaskell Ave., Erie, PA 16508. Not commercially available. Included for comparative purposes.
[13]Available commercially from Conoco Chemicals Company, P.O. Box 2197, Houston, TX 77001.
[14]Available commercially from Harshaw Chemical Company, 1945 East 97th Street, Cleveland, OH 44106.
[15]Available commercially from Kaiser Chemicals Company, 300 Lakeside Dr., Oakland, CA 94643.
[16]Available commercially from Akzo Armak Company (Agent), 300 So. Wacker Dr., Chicago, IL 60606.
[17]Available commercially from Norton Company, 1 New Bond St., Worcester, MA 01606.

EXAMPLES 2-43

General

A series of attrition resistant metal/oxygen compositions were prepared by intimately mixing the appropriate quantities of at least one metal oxide and an alumina, heating to a temperature and for a time sufficient to remove any added wetting agent and physically bound water, as well as other volatitle components, and calcining the mixture. The calcined material was cooled under controlled cool-down conditions and sieved to the size of the original alumina. The retained material accounted for greater than 90 weight percent of the calcined metal/oxygen composition. The metal/oxygen compositions were further characterized as described in Examples 44 (attrition rate) and 45 (transformation of agent (wet mixing process) and containing bismuth, calcium, and zirconium. (Example 3 is included as a comparative example to show an alumina outside the scope of the present invention.)

To a suitably sized wide-mouthed, polyethylene jar was added appropriate quantities of bismuth (III) oxide (Bi$_2$O$_3$), calcium oxide (CaO), and zirconium (IV) oxide (ZrO$_2$), all as powders, and a sufficient number of suitably sized alumdum balls [6-8 1.9-centimeter (0.75 inch) diameter for a 4.4-liter (1-gallon, dry) jar]. The jar was placed on a ball mill and the contents ball milled for 6 hours. The thoroughly mixed metal oxide powders and a sufficient quantity of the triply sieved alumina (in accordance with the procedure described in Example 1, above) were placed in a second suitably sized wide-mouthed, polyethylene jar without the alumdum balls.

The alumina/metal oxides mole percent ratio was approximately 55/45. The jar was shaken by hand for 5 minutes and then rotated on a ball mill for 3 hours. The resultant mixture was passed through a 100 mesh (U.S. Standard Sieve Size) screen to insure mixing. Any clumps remaining on the screen were broken up and passed through the screen. The sieved mixture was returned to the jar and rotated on the ball mill an additional 3 hours if any clumps remained on the screen after sieving, or, in the absence of any remaining clumps, for only 0.5 hour to break up any stratification of powders resulting from sieving.

To the dry-mixed components was added sufficient water, with stirring by hand, to form a thixotropic paste. The paste was placed in suitably sized fused alumina crucibles containing less than 0.2% silica to a maximum depth of 7.62 centimeters (3.0 inches). The loaded crucibles were placed in an air-purged furnace. The furnace was heated to 150°–250° C., usually 200° C., which temperature was maintained for 1 hour to 5 hours, usually 5 hours, to remove the excess wetting agent. The temperature was then increased to 1000° C. at a rate of 120° C. per hour (slow heat-up). Calcination was continued at 1000° C. for about 10 hours. After the calcination was complete, the metal/oxygen composition was cooled to 700° C. under controlled conditions at a maximum cool-down rate of 150° C. per hour. Thereafter, the cool-down was continued at its natural rate to ambient temperature.

The cooled, lightly agglomerated metal/oxygen composition was crushed and sieved for 30 minutes to complete the breakdown of the soft agglomerations to 120/400, 70/325, or 70/200 mesh particles, depending upon which corresponded to the original particle size of the alumina starting material. The retained material had a uniformly yellow color. The parameters for such compositions are set forth in Table 2, below.

EXAMPLES 11–19

The following is a general procedure for the preparation of a metal/oxygen composition in the absence of a wetting agent (dry mixing process) and containing lead, antimony, and bismuth. (Example 12 is included as a comparative example to show an alumina outside the scope of the present invention.)

The procedure described above for the wet mixing process (Examples 2–10) was employed through the dry-mixing steps using appropriate quantities of lead (II) oxide (PbO), antimony (III) oxide ($Sb_2O_3$), bismuth (III) oxide ($Bi_2O_3$), and alumina. The alumina/metal oxides mole percent ratio was 51.3/48.7. The thoroughly mixed components were placed in suitably sized fused alumina crucibles containing less than 0.2% silica and compacted to insure close physical contact. The maximum depth of loading was 7.62 centimeters (3.0 inches) to permit air to diffuse the material located at the bottom of the crucible during the air calcination. The loaded crucibles were placed in a nitrogen-purged furnace. The furnace, under a constant nitrogen purge, was heated to 150°–250° C., usually 200° C., which temperature was maintained for 1 hour to 5 hours, usually 2 hours, to remove any physically bound water. The temperature was then increased to 1000° C. over a 1-hour period (rapid heat-up) in order to delay the oxidation of antimony (III) oxide to antimony (V) oxide until the air calcination period. Calcination was continued at 1000° C. under a nitrogen purge for about 1 hour. The furnace atmosphere was changed to air and calcination continued under an air purge for an additional 9 hours. The calcined metal/oxygen composition, a uniformly burnt orange color, was then treated as described in Examples 2–10, above. The parameters for such compositions are set forth in Table 2, below.

EXAMPLES 20–34

The following illustrates the preparation of a number of metal/oxygen compositions containing a number of different elements.

The metal/oxygen compositions were prepared according to the wet mixing process procedure described in Examples 2–10, above, except that rapid heat-up to the calcination temperature as described in Examples 11–19, above, was employed for those compositions using antimony (III) oxide as a starting material. The parameters for such compositions are set forth in Table 2, below.

EXAMPLES 35–36

A number of metal/oxygen compositions were prepared according to the dry mixing process procedure described in Examples 11–19, above. The parameters for such compositions are set forth in Table 2, below.

EXAMPLE 37

The following procedures illustrate the preparation of a metal/oxygen composition containing bismuth. The parameters for such compositions are set forth in Table 2, below.

Procedure A—Bismuth (III) oxide ($Bi_2O_3$, 200.7 grams, 0.43 mole) was ball milled for 6 hours and dry mixed with 97.2 grams (0.90 mole) of 120/400 mesh alumina (Sample No. 1-F) as described in Examples 11–19, above. The $Al_2O_3/Bi_2O_3$ mole percent ratio was 67.7/32.3. The mixture was heated in air at 200° C. for 1 hour to remove any physically bound water, followed by 450° C. for 1 hour to remove any other volatile components, and then calcined at 850° C. for 5 hours. The metal/oxygen composition was cooled to 700° C. at a maximum cool-down rate of 150° C. per hour. Thereafter, the cool-down was continued at its natural rate to ambient temperature.

The cooled, lightly agglomerated metal/oxygen composition was crushed and sieved for 30 minutes to complete the breakdown of the soft agglomerations to −120 mesh particles. The metal/oxygen composition was then heated in air at 200° C. for 1 hour, followed by 450° C. for 1 hour to remove, respectively, any physically bound water and other volatile components, and recalcined at 850° C. for 1 hour and 1000° C. for 4 hours. Cool-down was carried out as previously described. The material was crushed and sieved for 30 minutes to complete the break-down of the soft agglomeration to 120/400 mesh particles which particle size corresponds to the original particle size range of the alumina.

Procedure B—Procedure A, above, was repeated except that the materials were wet mixed and dried as described in Examples 2–10, above.

Procedure C—Procedure A, above was repeated except that after the initial heating, calcination, cool-down, and sieving, the metal/oxygen composition was heated at 200° C. for 1 hour, followed by 450° C. for 1 hour to remove, respectively, any physically bound water and other volatile components, and calcined at 650° C. for 1.5 hours, 850° C. for 1.5 hours, and 900° C. for 4 hours.

Procedure D—Procedure A, above, was repeated using 200.0 grams (0.43 mole) of $Bi_2O_3$ and 86.0 grams (0.80 mole) of 120/400 mesh $Al_2O_3$ (Sample 1-F). The $Al_2O_3/Bi_2O_3$ mole percent ratio was 65/35.

Procedure E—A metal/oxygen composition having an $Al_2O_3/Bi_2O_3$ mole percent ratio of 69.7/30.3 was prepared in accordance with Procedure A, above, using 186.4 grams (0.40 mole) of $Bi_2O_3$ and 98.4 grams (0.92 mole) of 120/400 mesh $Al_2O_3$ (Sample 1-F).

Procedure F—A metal/oxygen composition having an $Al_2O_3/Bi_2O_3$ mole percent ratio of 66/34 was prepared in accordance with Procedure B, above, using 400.0 grams (0.86 mole) of $Bi_2O_3$ and 179.8 grams (1.67 moles) of 120/400 mesh $Al_2O_3$ (Sample 1-F).

EXAMPLE 38

The following procedures illustrate the preparation of metal/oxygen compositions containing bismuth, potassium, and zirconium. The parameters for such compositions are tabulated in Table 2, below.

Procedure A—An aqueous solution of 3.9 grams (0.070 mole) of potassium hydroxide (KOH) dissolved in the minimum amount of water was slurried with 24.3 grams (0.23 mole) of 120/400 mesh alumina (Sample No. 1-F) and heated to dryness. The dry mixture was dry-mixed with 48.9 grams (0.10 mole) of bismuth (III) oxide ($Bi_2O_3$) and 1.7 grams (0.014 mole) of zirconium (IV) oxide ($ZrO_2$) as described in Examples 11-19, above. The $Al_2O_3$/metal oxides mole percent ratio was 54.9/45.1. The dry mixture was heated in air at 500° C. for 1 hour to remove any physically bound water and other volatile components and calcined at 750° C. for 1 hour and 1000° C. for 9 hours. The metal/oxygen composition was cooled to ambient temperature and sieved as described in Example 37, Procedure A, above.

Procedure B—Procedure A, above, was repeated except that the materials were wet-mixed and dried as described in Examples 2-10, above. The dry mixture was heated in air at 500° C. for 1 hour to remove any physically bound water and other volatile components and then calcined at 1000° C. for 10 hours.

Procedure C—To an aqueous solution of 3.9 grams (0.070 mole) of potassium hydroxide dissolved in the minimum amount of water was added a previously ball-milled mixture of 48.9 grams (0.10 mole of bismuth (III) oxide and 1.7 grams (0.014 mole) of zirconium (IV) oxide and thoroughly mixed. The mixture was heated to dryness at 200° C. in an air-purged furnace over a 2-hour period, followed by further heating at 450° C. for 1 hour and 600° C. for 16 hours. The resultant material was ground to a very fine powder and dry mixed with 24.3 grams (0.23 mole) of 120/400 mesh alumina (Sample No. 1-F) as described in Examples 11-19, above. The mixture was heated at 450° C. for 1 hour to remove any physically bound water and other volatile components, and thereafter calcined in air at 750° C. for 0.5 hour, followed by 1000° C. for 10 hours.

EXAMPLE 39

The following procedure illustrates the preparation of a metal/oxygen composition containing bismuth, calcium, and zirconium. The parameters for the composition are tabulated in Table 2, below.

To an aqueous slurry of 48.9 grams (0.105 mole) of bismuth (III) oxide, 3.9 grams (0.070 mole) of calcium oxide, and 1.7 grams (0.014 mole) of zirconium (IV) oxide, which had been previously dry mixed as described in Examples 11-19, above, was added 24.3 grams (0.23 mole) of 120/400 mesh alumina (Sample No. 1-F). The $Al_2O_3$/metal oxides mole percent ratio was 54.9/45.1. The slurry was heated to dryness as described in Examples 2-10, above, and thereafter heated at 450° C. for 1 hour to remove any volatile components present. The mixture was then calcined at 1000° C. for 10 hours. The composition was cooled and sieved as described in Examples 2-10, above.

EXAMPLE 40

The following procedure illustrates the preparation of a metal/oxygen composition containing bismuth, potassium, and zirconium, and using methanol as a wetting agent. The parameters of the composition are set forth in Table 2, below.

To a methanolic solution of 101.9 grams (1.55 moles) of 85% potassium hydroxide (KOH) dissolved in 400 milliliters of methanol was added a dry mixed mixture (prepared as described in Examples 11-19, above) of reagent grade bismuth (III) oxide ($Bi_2O_3$, 1269.7 grams, 2.72 moles) zirconium (IV) oxide ($ZrO_2$, 44.8 grams, 0.36 mole), and 120/400 mesh alumina ($Al_2O_3$, 634.8 grams, 5.90 moles, Sample No. 1-F) to form a thixotropic paste. Sufficient methanol was added to ensure good mixing. The $Al_2O_3$/metal oxides mole percent ratio was 56.1/43.9. The paste was loaded into suitably sized fused alumina crucibles and placed in an air-purged furnace. The paste was heated to 970° C. at the rate of 2° C. per minute (slow heat-up). Calcination was continued at 970° C. for 10 hours. After the calcination was complete, the metal/oxygen composition was cooled to ambient temperatures and sieved to 120/400 mesh particles as described in Examples 2-10, above.

EXAMPLE 41

The following procedure illustrates the preparation of a metal/oxygen composition containing bismuth, potassium, and zirconium.

To an aqueous solution of 101.1 grams (1.00 mole) of potassium nitrate dissolved in 1000 milliliters of water was added a dry mixed mixture (prepared as described in Examples 11-19 above) of reagent grade bismuth (III) oxide ($Bi_2O_3$, 1398,0 grams, 3.00 moles), zirconium (IV) oxide ($ZrO_2$, 49.3 grams, 0.40 mole), and 120/400 mesh alumina ($Al_2O_3$, 738.2 grams, 6.19 moles, Sample No. 1-H) to form a thixotropic paste. Sufficient water was added to ensure good mixing. The $Al_2O_3$/metal oxides mole percent ratio was 56.6/43.4. The paste was loaded into suitably sized fused crucibles to about one-third capacity and placed in an air-purged furnace. The paste was dried at 200° C. for 5 hours and calcined at 1000° C. for 10 hours, and the composition cooled to ambient temperatures and sieved to 120/400 mesh particles as described in Examples 2-10, above.

EXAMPLE 42

The following procedure illustrates the preparation of a metal/oxygen composition containing bismuth, iron, calcium, and boron. The parameters for the composition are set forth in Table 2, below.

Reagent grade bismuth (III) oxide ($Bi_2O_3$, 233.2 grams, 0.50 mole), iron (III) oxide ($Fe_2O_3$, 80.0 grams, 0.50 mole), calcium oxide (CaO, 56.0 grams, 1.0 mole), boric acid ($H_3BO_3$, 12.4 grams, 0.20 mole) were thoroughly mixed by grinding together in a mortar. The resultant mixture was dry mixed with 160.0 grams (1.57 moles) of 120/400 mesh alumina (Sample 1-F) by physically stirring until a uniform mixture was obtained. The Al₂O₃/metal oxides mole percent ratio was 41.6/58.4. The mixture was divided equally among four 7.62-centimeter (3.0-inch) diameter and 2.54-centimeter (1.0-inch) deep fused alumina dishes containing less than 0.2% silica and having a capacity of about 80 milliliters. The material was compacted to ensure close physical contact. The shallow loading depth permitted air to diffuse the material located at the bottom of the dishes during the air calcination.

The loaded dishes were placed in an air-purged furnace and the mixture heated at 150° C. for 1 hour to remove any physically bound water, followed by 450° C. for 1 hour to remove any other volatile components. The mixture was then calcined at 750° C. for 1 hour, followed by 950° C. for 16 hours. The metal/oxygen composition was cooled to 700° C. at a maximum cool-down rate of 150° C. per hour and thereafter at its natural cool-down rate to ambient temperature.

The cooled, lightly agglomerated metal/oxygen composition was crushed and sieved for 30 minutes to complete the breakdown of the soft agglomerations to 120/400 mesh particles which corresponds to the original particle size range of the alumina.

EXAMPLE 43

The following procedure illustrates the preparation of a metal/oxygen composition containing bismuth, iron, and calcium, and using methanol as a wetting agent. The parameters for the composition are set forth in Table 2, below.

Reagent grade bismuth (III) oxide ($Bi_2O_3$, 58.3 grams, 0.125 mole), iron (III) oxide ($Fe_2O_3$, 20.0 grams, 0.125 mole), and calcium oxide (CaO, 14.0 grams, 0.25 mole) as the metal oxides and 120/400 mesh alumina ($Al_2O_3$, 40.0 grams, 0.39 mole, Sample No. 1-F) were thoroughly mixed as described in Example 40, above. The $Al_2O_3$/metal oxide mole percent ratio was 44/56. To the dry-mixed components was added sufficient methanol, with stirring by hand, to form a thixotropic paste. The paste was placed into a 7.62-centimeter (3.0 inch) diameter and 2.54-centimeter (1.0-inch) deep fused alumina dish containing less than 0.2% silica and having a capacity of 80 milliliters. The paste was heated, with stirring, to dryness on a hotplate. The shallow loading depth of the dry material permitted air to diffuse the material located at the bottom of the dish during air calcination. The loaded dish was placed in an air-purged furnace and the mixture heated, calcined to form the metal/oxygen composition, cooled, and sieved as described in Example 42, above.

EXAMPLE 44

This Example illustrates the accelerated attrition test used to determine attrition rate of the attrition resistant metal/oxygen compositions of this invention.

The apparatus used to determine the attrition rate is described in Houdry Catalyst Brochure, Air Products and Chemicals, Inc., "FCC Catalyst Retention is Better with Houdry® HFZ ™ & HEZ ™ Catalysts," 1977. It consisted of a stainless steel tube 69.85 centimeters (27.5 inches) in length and 3.81 centimeters (1.5 inches) in inside diameter connected through a cone [10.16-centimeter (4-inch) rise] to a stainless steel tube 45.72 centimeters (18 inches) in length and 12.7 centimeters (5 inches) in inside diameter which had a flanged opening at the upper end.

The upper end was capped with a 0.64-centimeter (0.25-inch) thick stainless steel plate having a tubular opening in the center 3.81 centimeters (1.5 inches) in length and 0.95 centimeter (0.38 inch) in inside diameter. The plate was bolted onto the flange through eight 0.48-centimeter (0.19-inch) diameter holes machined into its outer perimeter and sealed with a neoprene gasket. Attached to the center-tube opening was a 250-milliliter filter flask, which had an extraction thimble attached to its side arm. A perforated stainless steel plate containing three equally spaced 0.041-centimeter (0.016-inch) diameter holes was located at the bottom of the stainless steel tube. Connected to the bottom of the stainless steel tube was air inlet means containing pressure regulators and flow controllers. The filter flask and the extraction thimble assembly was conditioned by passing humidified air through it for 30 minutes and then weighed. A sample of the composition (from Examples 2–43) was screened using a 125/400 mesh sieve (U.S. Standard Sieve Size) to remove any dust and fines. A 50-milliliter sample of the screened composition was accurately weighed and charged to the apparatus described above. Humidified air was introduced through the perforated plate at the bottom of the stainless steel tube at a linear velocity of about $3.048 \times 10^4$ cm/sec ($1 \times 10^3$ ft/sec) to fluidize the composition.

After 5 hours, the flask and thimble assembly (first flask and thimble assembly) was replaced with another conditioned flask and thimble assembly (second flask and thimble assembly). The first flask and thimble assembly was weighed to determine the weight in grams of dust and fines associated with weak particles, dust, and trash already present in the composition. The fluidization was continued for an additional 16 hours for a total of 21 hours. At the end of this period, the second flask and thimble assembly was weighed to determine the weight in grams of dust and fines resulting from attrition during the prolonged fluidization. The attrition rate, as weight percent/hour, was calculated as follows:

$$\% \text{ Attrition} = \frac{\text{Dust \& Fines (5–21 Hr. Period), g}}{\text{Initial Weight, g} - \text{Dust \& Fines (0–5 Hr. Period), g}} \times 100$$

$$\text{Attrition rate} = \frac{\% \text{ Attrition}}{\text{Time Period, Hours}}$$

The attrition rate is shown in Table 2 under the column headed "Attrition Rate, Wt. % Hour."

TABLE 2

| | METAL OXIDE(S) | | | | | ALUMINA[1] | | | PARTICLE SIZE, μm[2] | |
|---|---|---|---|---|---|---|---|---|---|---|
| EX- | | | | | MEAN PARTICLE | | | | | |
| AMPLE | GRAMS | (MOLES) | | MOLE % | SIZE, μm[2] | GRAMS | (MOLES) | MOLE % | RANGE | MEAN |
| 2 | 201.7 | (0.43) | $Bi_2O_3$ | 24.9 | 10 | 103.1 | 1-A (0.95) | 55.0 | 38–125 | 90 |
| | 16.2 | (0.29) | CaO | 16.8 | 6 | 9.5[6] | | | | |
| | 7.1 | (0.058) | $ZrO_2$ | 3.4 | 4 | | | | | |
| 3* | | | " | " | " | 97.4 | 1-B (0.95) | " | " | 56 |

Procedure D—Procedure A, above, was repeated using 200.0 grams (0.43 mole) of $Bi_2O_3$ and 86.0 grams (0.80 mole) of 120/400 mesh $Al_2O_3$ (Sample 1-F). The $Al_2O_3/Bi_2O_3$ mole percent ratio was 65/35.

Procedure E—A metal/oxygen composition having an $Al_2O_3/Bi_2O_3$ mole percent ratio of 69.7/30.3 was prepared in accordance with Procedure A, above, using 186.4 grams (0.40 mole) of $Bi_2O_3$ and 98.4 grams (0.92 mole) of 120/400 mesh $Al_2O_3$ (Sample 1-F).

Procedure F—A metal/oxygen composition having an $Al_2O_3/Bi_2O_3$ mole percent ratio of 66/34 was prepared in accordance with Procedure B, above, using 400.0 grams (0.86 mole) of $Bi_2O_3$ and 179.8 grams (1.67 moles) of 120/400 mesh $Al_2O_3$ (Sample 1-F).

EXAMPLE 38

The following procedures illustrate the preparation of metal/oxygen compositions containing bismuth, potassium, and zirconium. The parameters for such compositions are tabulated in Table 2, below.

Procedure A—An aqueous solution of 3.9 grams (0.070 mole) of potassium hydroxide (KOH) dissolved in the minimum amount of water was slurried with 24.3 grams (0.23 mole) of 120/400 mesh alumina (Sample No. 1-F) and heated to dryness. The dry mixture was dry-mixed with 48.9 grams (0.10 mole) of bismuth (III) oxide ($Bi_2O_3$) and 1.7 grams (0.014 mole) of zirconium (IV) oxide ($ZrO_2$) as described in Examples 11-19, above. The $Al_2O_3$/metal oxides mole percent ratio was 54.9/45.1. The dry mixture was heated in air at 500° C. for 1 hour to remove any physically bound water and other volatile components and calcined at 750° C. for 1 hour and 1000° C. for 9 hours. The metal/oxygen composition was cooled to ambient temperature and sieved as described in Example 37, Procedure A, above.

Procedure B—Procedure A, above, was repeated except that the materials were wet-mixed and dried as described in Examples 2-10, above. The dry mixture was heated in air at 500° C. for 1 hour to remove any physically bound water and other volatile components and then calcined at 1000° C. for 10 hours.

Procedure C—To an aqueous solution of 3.9 grams (0.070 mole) of potassium hydroxide dissolved in the minimum amount of water was added a previously ball-milled mixture of 48.9 grams (0.10 mole of bismuth (III) oxide and 1.7 grams (0.014 mole) of zirconium (IV) oxide and thoroughly mixed. The mixture was heated to dryness at 200° C. in an air-purged furnace over a 2-hour period, followed by further heating at 450° C. for 1 hour and 600° C. for 16 hours. The resultant material was ground to a very fine powder and dry mixed with 24.3 grams (0.23 mole) of 120/400 mesh alumina (Sample No. 1-F) as described in Examples 11-19, above. The mixture was heated at 450° C. for 1 hour to remove any physically bound water and other volatile components, and thereafter calcined in air at 750° C. for 0.5 hour, followed by 1000° C. for 10 hours.

EXAMPLE 39

The following procedure illustrates the preparation of a metal/oxygen composition containing bismuth, calcium, and zirconium. The parameters for the composition are tabulated in Table 2, below.

To an aqueous slurry of 48.9 grams (0.105 mole) of bismuth (III) oxide, 3.9 grams (0.070 mole) of calcium oxide, and 1.7 grams (0.014 mole) of zirconium (IV) oxide, which had been previously dry mixed as described in Examples 11-19, above, was added 24.3 grams (0.23 mole) of 120/400 mesh alumina (Sample No. 1-F). The $Al_2O_3$/metal oxides mole percent ratio was 54.9/45.1. The slurry was heated to dryness as described in Examples 2-10, above, and thereafter heated at 450° C. for 1 hour to remove any volatile components present. The mixture was then calcined at 1000° C. for 10 hours. The composition was cooled and sieved as described in Examples 2-10, above.

EXAMPLE 40

The following procedure illustrates the preparation of a metal/oxygen composition containing bismuth, potassium, and zirconium, and using methanol as a wetting agent. The parameters of the composition are set forth in Table 2, below.

To a methanolic solution of 101.9 grams (1.55 moles) of 85% potassium hydroxide (KOH) dissolved in 400 milliliters of methanol was added a dry mixed mixture (prepared as described in Examples 11-19, above) of reagent grade bismuth (III) oxide ($Bi_2O_3$, 1269.7 grams, 2.72 moles) zirconium (IV) oxide ($ZrO_2$, 44.8 grams, 0.36 mole), and 120/400 mesh alumina ($Al_2O_3$, 634.8 grams, 5.90 moles, Sample No. 1-F) to form a thixotropic paste. Sufficient methanol was added to ensure good mixing. The $Al_2O_3$/metal oxides mole percent ratio was 56.1/43.9. The paste was loaded into suitably sized fused alumina crucibles and placed in an air-purged furnace. The paste was heated to 970° C. at the rate of 2° C. per minute (slow heat-up). Calcination was continued at 970° C. for 10 hours. After the calcination was complete, the metal/oxygen composition was cooled to ambient temperatures and sieved to 120/400 mesh particles as described in Examples 2-10, above.

EXAMPLE 41

The following procedure illustrates the preparation of a metal/oxygen composition containing bismuth, potassium, and zirconium.

To an aqueous solution of 101.1 grams (1.00 mole) of potassium nitrate dissolved in 1000 milliliters of water was added a dry mixed mixture (prepared as described in Examples 11-19 above) of reagent grade bismuth (III) oxide ($Bi_2O_3$, 1398,0 grams, 3.00 moles), zirconium (IV) oxide ($ZrO_2$, 49.3 grams, 0.40 mole), and 120/400 mesh alumina ($Al_2O_3$, 738.2 grams, 6.19 moles, Sample No. 1-H) to form a thixotropic paste. Sufficient water was added to ensure good mixing. The $Al_2O_3$/metal oxides mole percent ratio was 56.6/43.4. The paste was loaded into suitably sized fused crucibles to about one-third capacity and placed in an air-purged furnace. The paste was dried at 200° C. for 5 hours and calcined at 1000° C. for 10 hours, and the composition cooled to ambient temperatures and sieved to 120/400 mesh particles as described in Examples 2-10, above.

EXAMPLE 42

The following procedure illustrates the preparation of a metal/oxygen composition containing bismuth, iron, calcium, and boron. The parameters for the composition are set forth in Table 2, below.

Reagent grade bismuth (III) oxide ($Bi_2O_3$, 233.2 grams, 0.50 mole), iron (III) oxide ($Fe_2O_3$, 80.0 grams, 0.50 mole), calcium oxide (CaO, 56.0 grams, 1.0 mole), boric acid ($H_3BO_3$, 12.4 grams, 0.20 mole) were thoroughly mixed by grinding together in a mortar. The resultant mixture was dry mixed with 160.0 grams (1.57 moles) of 120/400 mesh alumina (Sample 1-F) by physically stirring until a uniform mixture was obtained. The Al$_2$O$_3$/metal oxides mole percent ratio was 41.6/58.4. The mixture was divided equally among four 7.62-centimeter (3.0-inch) diameter and 2.54-centimeter (1.0-inch) deep fused alumina dishes containing less than 0.2% silica and having a capacity of about 80 milliliters. The material was compacted to ensure close physical contact. The shallow loading depth permitted air to diffuse the material located at the bottom of the dishes during the air calcination.

The loaded dishes were placed in an air-purged furnace and the mixture heated at 150° C. for 1 hour to remove any physically bound water, followed by 450° C. for 1 hour to remove any other volatile components. The mixture was then calcined at 750° C. for 1 hour, followed by 950° C. for 16 hours. The metal/oxygen composition was cooled to 700° C. at a maximum cool-down rate of 150° C. per hour and thereafter at its natural cool-down rate to ambient temperature.

The cooled, lightly agglomerated metal/oxygen composition was crushed and sieved for 30 minutes to complete the breakdown of the soft agglomerations to 120/400 mesh particles which corresponds to the original particle size range of the alumina.

EXAMPLE 43

The following procedure illustrates the preparation of a metal/oxygen composition containing bismuth, iron, and calcium, and using methanol as a wetting agent. The parameters for the composition are set forth in Table 2, below.

Reagent grade bismuth (III) oxide (Bi$_2$O$_3$, 58.3 grams, 0.125 mole), iron (III) oxide (Fe$_2$O$_3$, 20.0 grams, 0.125 mole), and calcium oxide (CaO, 14.0 grams, 0.25 mole) as the metal oxides and 120/400 mesh alumina (Al$_2$O$_3$, 40.0 grams, 0.39 mole, Sample No. 1-F) were thoroughly mixed as described in Example 40, above. The Al$_2$O$_3$/metal oxide mole percent ratio was 44/56. To the dry-mixed components was added sufficient methanol, with stirring by hand, to form a thixotropic paste. The paste was placed into a 7.62-centimeter (3.0 inch) diameter and 2.54-centimeter (1.0-inch) deep fused alumina dish containing less than 0.2% silica and having a capacity of 80 milliliters. The paste was heated, with stirring, to dryness on a hotplate. The shallow loading depth of the dry material permitted air to diffuse the material located at the bottom of the dish during air calcination. The loaded dish was placed in an air-purged furnace and the mixture heated, calcined to form the metal/oxygen composition, cooled, and sieved as described in Example 42, above.

EXAMPLE 44

This Example illustrates the accelerated attrition test used to determine attrition rate of the attrition resistant metal/oxygen compositions of this invention.

The apparatus used to determine the attrition rate is described in Houdry Catalyst Brochure, Air Products and Chemicals, Inc., "FCC Catalyst Retention is Better with Houdry ® HFZ ™ & HEZ ™ Catalysts," 1977. It consisted of a stainless steel tube 69.85 centimeters (27.5 inches) in length and 3.81 centimeters (1.5 inches) in inside diameter connected through a cone [10.16-centimeter (4-inch) rise] to a stainless steel tube 45.72 centimeters (18 inches) in length and 12.7 centimeters (5 inches) in inside diameter which had a flanged opening at the upper end.

The upper end was capped with a 0.64-centimeter (0.25-inch) thick stainless steel plate having a tubular opening in the center 3.81 centimeters (1.5 inches) in length and 0.95 centimeter (0.38 inch) in inside diameter. The plate was bolted onto the flange through eight 0.48-centimeter (0.19-inch) diameter holes machined into its outer perimeter and sealed with a neoprene gasket. Attached to the center-tube opening was a 250-milliliter filter flask, which had an extraction thimble attached to its side arm. A perforated stainless steel plate containing three equally spaced 0.041-centimeter (0.016-inch) diameter holes was located at the bottom of the stainless steel tube. Connected to the bottom of the stainless steel tube was air inlet means containing pressure regulators and flow controllers. The filter flask and the extraction thimble assembly was conditioned by passing humidified air through it for 30 minutes and then weighed. A sample of the composition (from Examples 2–43) was screened using a 125/400 mesh sieve (U.S. Standard Sieve Size) to remove any dust and fines. A 50-milliliter sample of the screened composition was accurately weighed and charged to the apparatus described above. Humidified air was introduced through the perforated plate at the bottom of the stainless steel tube at a linear velocity of about $3.048 \times 10^4$ cm/sec ($1 \times 10^3$ ft/sec) to fluidize the composition.

After 5 hours, the flask and thimble assembly (first flask and thimble assembly) was replaced with another conditioned flask and thimble assembly (second flask and thimble assembly). The first flask and thimble assembly was weighed to determine the weight in grams of dust and fines associated with weak particles, dust, and trash already present in the composition. The fluidization was continued for an additional 16 hours for a total of 21 hours. At the end of this period, the second flask and thimble assembly was weighed to determine the weight in grams of dust and fines resulting from attrition during the prolonged fluidization. The attrition rate, as weight percent/hour, was calculated as follows:

$$\% \text{ Attrition} = \frac{\text{Dust \& Fines (5-21 Hr. Period), g}}{\text{Initial Weight, g} - \text{Dust \& Fines (0-5 Hr. Period), g}} \times 100$$

$$\text{Attrition rate} = \frac{\% \text{ Attrition}}{\text{Time Period, Hours}}$$

The attrition rate is shown in Table 2 under the column headed "Attrition Rate, Wt. % Hour."

TABLE 2

| | METAL OXIDE(S) | | | | | ALUMINA[1] | | | PARTICLE SIZE, μm$^2$ | |
|---|---|---|---|---|---|---|---|---|---|---|
| EX- AMPLE | GRAMS (MOLES) | | MOLE % | MEAN PARTICLE SIZE, μm$^2$ | | GRAMS (MOLES) | | MOLE % | RANGE | MEAN |
| 2 | 201.7 (0.43) | Bi$_2$O$_3$ | 24.9 | 10 | | 103.1 1-A | (0.95) | 55.0 | 38–125 | 90 |
| | 16.2 (0.29) | CaO | 16.8 | 6 | 9.5$^6$ | | | | | |
| | 7.1 (0.058) | ZrO$_2$ | 3.4 | 4 | | | | | | |
| 3* | | " | | " | " | 97.4 1-B | (0.95) | " | " | 56 |

TABLE 2-continued

| | | | | | | | | | | |
|---|---|---|---|---|---|---|---|---|---|---|
| 4 | | | | " | | " | " | 112.7 | 1-C (0.95) | " | " | 68 |
| 5 | | | | " | | " | " | 98.4 | 1-D (0.95) | " | " | 60 |
| 6 | | | | " | | " | " | 99.2 | 1-E (0.95) | " | " | 62 |
| 7 | | | | " | | " | " | 101.5 | 1-F (0.95) | " | " | 77 |
| 8 | | | | " | | " | " | 112.7 | 1-G (0.95) | " | " | 50 |
| 9 | | | | " | | " | " | 112.7 | 1-H (0.95) | " | " | 74 |
| 10 | | | | " | | " | " | 104.2 | 1-J (0.95) | " | " | 93 |
| 11 | 160.2 (0.72) | PbO | 38.9 | 8 | | | 103.1 | 1-A (0.95) | 51.3 | " | 90 |
| | 31.4 (0.11) | $Sb_2O_3$ | 5.9 | 3 | 7.6[6] | | | | | |
| | 33.4 (0.072) | $Bi_2O_3$ | 3.9 | 10 | | | | | | |
| 12* | | " | | " | " | | 97.4 | 1-B (0.95) | " $2O_3$ | " | 56 / 10 |
| 13 | | | | " | | " | " | 112.7 | 1-C (0.95) | " $2O_3$ | " | 68 / 10 |
| 14 | | " | | " | " | | 98.4 | 1-D (0.95) | " $2O_3$ | " | 60 / 10 |
| 15 | 160.2 (0.72) | PbO | 38.9 | 8 | | | 99.2 | 1-E (0.95) | 51.3 | 38-125 | 62 |
| | 31.4 (0.11) | $Sb_2O_3$ | 5.9 | 3 | 7.6[6] | | | | | |
| | 33.4 (0.072) | $Bi_2O_3$ | 3.9 | 10 | " | | | | | |
| 16 | | " | | " | " | | 101.5 | 1-F (0.95) | " $2O_3$ | " | 77 / 10 |
| 17 | | " | | " | " | | 112.7 | 1-G (0.95) | " $2O_3$ | " | 50 / 10 |
| 18 | | " | | " | " | | 112.7 | 1-H (0.95) | " $2O_3$ | " | 74 / 10 |
| 19 | | " | | " | " | | 104.2 | 1-J (0.95) | " $2O_3$ | " | 93 / 10 |
| 20 | 50.2 (0.22) | PbO | 36.4 | 8 | 7.2[6] | | 40.0 | 1-I (0.35) | 57.9 | 75-200 | 97 |
| | 9.8 (0.034) | $Sb_2O_3$ | 5.6 | 3 | | | | | | |
| 21 | 94.9 (0.20) | $Bi_2O_3$ | 27.4 | 10 | 9.2[6] | | 45.0 | 1-I (0.39) | 53.4 | " | 97 |
| | 10.1 (0.14) | NiO | 19.2 | 2[9] | | | | | | |
| 22 | 33.1 (0.44) | CoO | 41.9 | 5[9] | 5.0[6] | | 45.0 | 1-I (0.39) | 37.1 | " | 97 |
| | 71.9 (0.22) | $La_2O_3$ | 21.0 | 5[9] | | | | | | |
| 23 | 42.7 (0.19) | PbO | 31.4 | 8 | | | 40.0 | 1-I (0.35) | 57.8 | 45-200 | 93 |
| | 8.4 (0.029) | $Sb_2O_3$ | 4.8 | 3 | 7.6[6] | | | | | |
| | 8.9 (0.019) | $Bi_2O_3$ | 3.1 | 10 | | | | | | |
| | 1.0 (0.018) | KOH | 3.0 | —[10] | | | | | | |
| 24 | 42.7 (0.19) | PbO | 31.3 | 8 | | | 40.0 | 1-I (0.35) | 57.7 | 75-200 | 97 |
| | 8.4 (0.029) | $Sb_2O_3$ | 4.8 | 3 | 7.6[6] | | | | | |
| | 8.9 (0.019) | $Bi_2O_3$ | 3.1 | 10 | | | | | | |
| | 0.8 (0.019) | MgO | 3.1 | 7 | | | | | | |
| 25 | 42.7 (0.19) | PbO | 31.3 | 8 | | | 40.0 | 1-I (0.35) | 57.7 | " | " |
| | 8.4 (0.029) | $Sb_2O_3$ | 4.8 | 3 | 7.5[6] | | | | | |
| | 8.9 (0.019) | $Bi_2O_3$ | 3.1 | 10 | | | | | | |
| | 1.6 (0.019) | ZnO | 3.1 | 3 | | | | | | |
| 26 | 42.7 (0.19) | PbO | 31.3 | 8 | | | 40.1 | 1-I (0.35) | 57.7 | " | " |
| | 8.4 (0.029) | $Sb_2O_3$ | 4.8 | 3 | 7.6[6] | | | | | |
| | 8.9 (0.019) | $Bi_2O_3$ | 3.1 | 10 | | | | | | |
| | 0.5 (0.019) | LiOH | 3.1 | —[10] | | | | | | |
| 27 | 60.0 (0.27) | PbO | 43.5 | 8 | | | 40.0 | 1-I (0.35) | 56.5 | " | " |
| 28 | 49.6 (0.22) | PbO | 37.2 | " | 8.3[6] | | 40.0 | 1-I (0.35) | 59.1 | 45-200 | 93 |
| | 10.4 (0.022) | $Bi_2O_3$ | 3.7 | 10 | | | | | | |
| 29 | 113.9 (0.51) | PbO | 51.6 | 8 | | | 40.0 | 1-I (0.35) | 35.4 | 45-200 | 93 |
| | 22.3 (0.077) | $Sb_2O_3$ | 7.8 | 3 | 7.6[6] | | | | | |
| | 23.8 (0.051) | $Bi_2O_3$ | 5.2 | 10 | | | | | | |
| 30 | 26.7 (0.12) | PbO | 32.4 | 8 | | | 25.0 | 1-I (0.22) | 59.5 | 38-125 | 93 |
| | 5.2 (0.018) | $Sb_2O_3$ | 4.9 | 3 | 7.6[6] | | | | | |
| | 5.6 (0.012) | $Bi_2O_3$ | 3.2 | 10 | | | | | | |
| 31 | 17.9 (0.080) | PbO | 25.0 | 8 | | | 25.1 | 1-I (0.22) | 68.8 | " | 93 |
| | 3.5 (0.012) | $Sb_2O_3$ | 3.8 | 3 | 7.6[6] | | | | | |
| | 3.7 (0.0080) | $Bi_2O_3$ | 2.5 | 10 | | | | | | |
| 32 | 285.7 (1.28) | PbO | 41.4 | 8 | | | 172.2 | 1-I (1.49) | 48.2 | 75-200 | 97 |
| | 56.0 (0.19) | $Sb_2O_3$ | 6.1 | 3 | " | | | | | |
| | 59.6 (0.13) | $Bi_2O_3$ | 4.2 | 10 | | | | | | |
| 33 | 42.7 (0.19) | PbO | 32.3 | 8 | | | 40.0 | 1-I (0.35) | 59.5 | 45-200 | 93 |
| | 8.4 (0.029) | $Sb_2O_3$ | 4.9 | 3 | " | | | | | |
| | 8.9 (0.019) | $Bi_2O_3$ | 3.2 | 10 | | | | | | |
| 34 | 74.5 (0.33) | PbO | 41.1 | 8 | | | 45.0 | 1-I (0.39) | 48.6 | 75-200 | 97 |
| | 14.6 (0.050) | $Sb_2O_3$ | 6.2 | 3 | 7.6[6] | | | | | |
| | 15.6 (0.033) | $Bi_2O_3$ | 4.1 | 10 | | | | | | |
| 35 | 74.5 (0.33) | PbO | 41.1 | 8 | | | 45.0 | 1-I (0.39) | 48.6 | " | " |
| | 14.6 (0.050) | $Sb_2O_3$ | 6.2 | 3 | " | | | | | |
| | 15.6 (0.033) | $Bi_2O_3$ | 4.1 | 10 | | | | | | |
| 36 | 74.5 (0.33) | PbO | 41.1 | 8 | | | 45.0 | 1-I | 48.6 | 75-200 | 97 |

TABLE 2-continued

|  | 14.6 (0.050) | Sb$_2$O$_3$ | 6.2 | 3 | 7.6[6] | (0.39) |  |  |  |
|---|---|---|---|---|---|---|---|---|---|
|  | 15.6 (0.033) | Bi$_2$O$_3$ | 4.1 | 10 |  |  |  |  |  |
| 37-A | 200.7 (0.43) | Bi$_2$O$_3$ | 32.3 | " |  | 97.2 1-F (0.90) | 67.7 | 38–125 | " |
| 37-B |  | " |  | " |  | " |  | " | " |
| 37-C |  | " |  | " |  | " |  | " | " |
| 37-D | 200.0 (0.43) | " | 35.0 | " |  | 86.0 1-F (0.80) | 65.0 | " | " |
| 37-E | 186.4 (0.40) | " | 30.3 | " |  | 98.4 1-F (0.92) | 69.7 | " | " |
| 37-F | 400.0 (0.86) | " | 34.0 | " |  | 179.8 1-F (1.67) | 66.0 | " | " |
| 38-A | 48.9 (0.105) | " | 25.1 | " |  | 24.3 1-F (0.23) | 54.9 | " | " |
|  | 3.9 (0.070) | KOH | 16.7 | —[10] | 9.8 |  |  |  |  |
|  | 1.7 (0.014) | ZrO$_2$ | 3.3 | 4 |  |  |  |  |  |
| 38-B |  | " |  | " | " | " |  | " | " |
| 38-C |  | " |  | " | " | " |  | " | " |
| 39 | 48.9 (0.105) | Bi$_2$O$_3$ | 25.1 | 10 |  | 24.3 1-F (0.23) | 54.9 | 38–125 | 77 |
|  | 3.9 (0.070) | CaO | 16.7 | 6 | 9.5[6] |  |  |  |  |
|  | 1.7 (0.014) | ZrO$_2$ | 3.3 | 4 |  |  |  |  |  |
| 40 | 1269.7 (2.72) | Bi$_2$O$_3$ | 25.8 | 10 |  | 634.8 1-F (5.90) | 56.1 | 38–125 | 77 |
|  | 44.8 (0.36) | ZrO$_2$ | 3.4 | 4 | 9.8[6] |  |  |  |  |
|  | 101.9 (1.55) | KOH (85%) | 14.7 | —[10] |  |  |  |  |  |
| 41 | 1398.0 (3.00) | Bi$_2$O$_3$ | 29.6 | 10 |  | 738.2 1-H[11] (5.73) | 56.6 | " | 74 |
|  | 49.3 (0.40) | ZrO$_2$ | 3.9 | 4 | " |  |  |  |  |
|  | 101.1 (1.00) | KNO$_3$ | 9.9 | —[10] |  |  |  |  |  |
| 42 | 233.2 (0.50) | Bi$_2$O$_3$ | 13.3 | 2[9] |  | 160.0 1-F (1.57) | 41.6 | " | " |
|  | 80.0 (0.50) | Fe$_2$O$_3$ | 13.3 | 5.5[9] | 2.7[6] |  |  |  |  |
|  | 56.0 (1.00) | CaO | 26.5 | 1.5[9] |  |  |  |  |  |
|  | 12.4 (0.20) | H$_3$BO$_3$ | 5.3 | 3.5[9] |  |  |  |  |  |
| 43 | 58.3 (0.125) | Bi$_2$O$_3$ | 14.0 | 2[9] |  | 40.0 1-F (0.39) | 44.0 | " | " |
|  | 20.0 (0.125) | Fe$_2$O$_3$ | 14.0 | 5.5[9] | " |  |  |  |  |
|  | 14.0 (0.25) | CaO | 28.0 | 1.5[9] |  |  |  |  |  |

| EXAMPLE | ALUMINA/METAL OXIDE(S) MEAN PARTICLE SIZE RATIO | PREPARATIVE CONDITIONS TEMPERATURE, °C./TIME, HOURS DRYING | CALCINATION | ATTRITION RATE[3] WT. %/ HOUR | SURFACE AREA[4] m$^2$/g | METAL/OXYGEN COMPOSITION EMPIRICAL FORMULA[5] |
|---|---|---|---|---|---|---|
| 2 | 9.5 | 200/5[7] | 1000/10[7] | 0.21 | 0.15 | Bi$_{15}$Ca$_5$ZrO$_x$(Al$_2$O$_3$)$_{16}$ |
| 3* | 5.9 | " | " | 0.42 | 0.09 | " |
| 4 | 7.2 | " | " | 0.36 | 0.08 | " |
| 5 | 6.3 | " | " | 0.21 | 0.22 | " |
| 6 | 6.5 | " | " | 0.30 | 0.16 | " |
| 7 | 8.1 | " | " | 0.19 | 0.09 | " |
| 8 | 5.3 | " | " | 0.23 | 0.15 | " |
| 9 | 7.8 | " | " | 0.30 | 0.17 | " |
| 10 | 9.8 | " | " | 0.23 | 0.09 | " |
| 11 |  | 200/2[8] | (1)1000/1[8] (2)1000/9[7] | 0.19 | 0.52 | Pb$_{10}$Sb$_3$Bi$_2$O$_x$(Al$_2$O$_3$)$_{13}$ |
| 12* | 7.4 | " | " | 0.50 | 1.97 | " |
| 13 | 8.9 | " | " | 0.41 | 0.52 | " |
| 14 | 7.9 | " | " | 0.39 | 0.30 | " |
| 15 | 8.2 | " | (1)1000/1[8] (2)1000/9[7] | 0.30 | 0.40 | " |
| 16 | 10.1 | " | " | 0.16 | 0.16 | " |
| 17 | 6.6 | " | " | 0.21 | 0.54 | " |
| 18 | 9.7 | " | " | 0.13 | 0.35 | " |
| 19 | 12.2 | " | " | 0.26 | 0.20 | " |
| 20 | 13.5 | " | 1000/10[8] | 0.75 | 3.15 | Pb$_{10}$Sb$_3$O$_x$(Al$_2$O$_3$)$_{15}$ |
| 21 | 10.5 | " | " | 0.26 | 0.11 | Bi$_3$NiO$_x$(Al$_2$O$_3$)$_3$ |
| 22 | 19.4 | " | " | 0.54 | >5 | CoLaO$_x$(Al$_2$O$_3$) |
| 23 | 12.2 | " | " | 0.17 | 1.54 | Pb$_{10}$Sb$_3$Bi$_2$KO$_x$(Al$_2$O$_3$)$_{19}$ |
| 24 | 12.8 | 250/2[8] | " | 0.80 | 1.48 | Pb$_{10}$Sb$_3$Bi$_2$MgO$_x$(Al$_2$O$_3$)$_{18}$ |
| 25 | 12.9 | " | " | 0.50 | 1.67 | Pb$_{10}$Sb$_3$Bi$_2$ZnO$_x$(Al$_2$O$_3$)$_{18}$ |
| 26 | 12.8 | " | " | 0.53 | 1.82 | Pb$_{10}$Sb$_3$Bi$_2$LiO$_x$(Al$_2$O$_3$)$_{18}$ |
| 27 | 12.1 | 200/2[8] | 1000/2[8] | 0.27 | 0.36 | (PbO$_x$)$_3$(Al$_2$O$_3$)$_4$ |
| 28 | 11.2 | 250/2[8] | 1000/10[8] | 0.18 | 0.71 | Pb$_5$BiO$_x$(Al$_2$O$_3$)$_{18}$ |
| 29 | 12.2 | 200/2[8] | " | 0.13 | 0.46 | Pb$_{10}$Sb$_3$Bi$_2$O$_x$(Al$_2$O$_3$)$_7$ |
| 30 | " | 150/2[8] | " | 0.25 | 0.69 | Pb$_{10}$Sb$_3$Bi$_2$O$_x$(Al$_2$O$_3$)$_{18}$ |
| 31 | " | 200/2[8] | " | 0.70 | 2.3 | Pb$_{10}$Sb$_3$Bi$_2$O$_x$(Al$_2$O$_3$)$_{28}$ |
| 32 | " | 250/2[8] | " | 0.32 | 0.54 | Pb$_{10}$Sb$_3$Bi$_2$O$_x$(Al$_2$O$_3$)$_{12}$ |
| 33 | " | 200/2[8] | 900/10[8] | 0.10 | 0.69 | Pb$_{10}$Sb$_3$Bi$_2$O$_x$(Al$_2$O$_3$)$_{18}$ |
| 34 | " | 250/2[7] | 1000/10[7] | 0.38 | 0.33 | Pb$_{10}$Sb$_3$Bi$_2$O$_x$(Al$_2$O$_3$)$_{12}$ |
| 35 | " | 250/2[8] | 1000/10[8] | 0.37 | 0.26 | Pb$_{10}$Sb$_3$Bi$_2$O$_x$(Al$_2$O$_3$)$_{12}$ |
| 36 | " | 250/2[8] | 1000/10[7] | 0.29 | 0.34 | Pb$_{10}$Sb$_3$Bi$_2$O$_x$(Al$_2$O$_3$)$_{12}$ |
| 37-A | 9.7 | (1)200/1[7] (2)450/1[7] (4)200/1[7] (5)450/1[7] | (3) 850/5[7] (6) 850/1[7] (7)1000/4[7] | 0.35 | 0.17 | BiO$_x$(Al$_2$O$_3$) |
| 37-B | " | " | " | 0.32 | 0.22 | " |
| 37-C | " | (1)200/1[7] | (3) 650/1.5[7] | 0.30 | 0.15 | " |

TABLE 2-continued

| | | | | | | |
|---|---|---|---|---|---|---|
| 37-D | 9.9 | (1)200/1[7]<br>(2)450/1[7]<br>(4)200/1[7]<br>(5)450/1[7] | (2)450/1[7]<br>(5) 900/4[7]<br>(3) 850/5[7]<br>(6) 850/1[7]<br>(7)1000/4[7] | (4) 450/1.5[7]<br>0.63 | 0.20 | $BiO_x(Al_2O_3)_{0.93}$ |
| 37-E | " | " | " | 0.22 | 0.20 | $BiO_x(Al_2O_3)_{1.15}$ |
| 37-F | " | " | " | 0.29 | 0.15 | $BiO_x(Al_2O_3)_{0.97}$ |
| 38-A | " | (1)500/1[7]<br>(3)1000/9[7] | (2) 759/1[7] | 0.20 | 0.20 | $Bi_{15}K_5ZrO_x(Al_2O_3)_{16}$ |
| 38-B | " | (1)200/5[7]<br>(2)500/1[7] | (3)1000/10[7] | 0.16 | " | " |
| 38-C | " | (1)200/2[7]<br>(2)450/1[7] | (3) 750/0.5[7]<br>(4)1000/10[7] | 0.38 | 0.12 | " |
| 39 | 8.1 | (1)200/5[7]<br>(2)450/1[7] | (3)1000/10[7] | 0.25 | 0.35 | $Bi_{15}Ca_5ZrO_x(Al_2O_3)_{16}$ |
| 40 | 7.9 | 970[7] | 970/10[7] | 0.19 | 0.22 | $Bi_{15}K_4ZrO_x(Al_2O_3)_{16}$ |
| 41 | 7.6 | 200/5[7] | 1000/10[7] | 0.10 | 0.25 | $Bi_{30}K_5Zr_2O_x(Al_2O_3)_{29}$ |
| 42 | 28.5 | (1)150/1[7] | (3) 750/1[7] | 0.23 | 0.21 | $Bi_5Fe_5Ca_5BO_x(Al_2O_3)_8$ |
| 43 | 28.5 | (1)150/1[7]<br>(2)450/1[7] | (3) 750/1[7]<br>(4) 950/16[7] | 0.33 | 0.18 | $Bi_2Fe_2Ca_2O_x(Al_2O_3)_3$ |

[1]Alumina Sample No. from Table 1.
[2]Measured according to the manufacturer's procedure using a Leeds & Northrup Microtrak instrument unless specified otherwise.
[3]Determined by the accelerated attrition test as described in Example 44.
[4]Measured according to ASTM D 3663-78 for surface area of catalysts using a Micromeritics Digisorb 2500 instrument.
[5]The empirical formula, for convenience only, is written showing alumina units associated with the remaining components. The alumina, however, is an integral component of the infusion and reaction product. Subscript "x" is a number taken to satisfy the average valences of the metal elements (excluding aluminum) in the oxidation states in which they exist in the compositions.
[6]Calculated weight average.
[7]Air atmosphere.
[8]Nitrogen atmosphere.
[9]Measured by viewing on a calibrated grid using a microscope.
[10]Dissolved and used as a solution.
[11]Sample contained 20.8 weight % water.
[12]Slow heat up at the rate of 2° C./minute.
*Comparative example using an alumina outside the scope of the present invention.

EXAMPLE 45

A. Toluene Converstion Reactor—A fluidized bed reactor was employed unless otherwise noted, in which case a fixed bed reactor was employed.

(1) Fluidized Bed—A stainless steel tube 38.1 centimeters (15 inches) in length and 1.27 centimeters (0.5 inch) outside diameter was employed as a fluidized bed reactor for the toluene conversion reaction. The tube was capped on the bottom by a conical section that had a 30° angle. The reactor was arranged vertically and equipped at the lower end with reactant inlet means for introducing the feed materials. The inlet means was fitted with a porous metal frit for gas dispersion. The reactor was equipped at the upper end with reaction effluent outlet means fitted with a 90 μm filter, for collecting the effluent or, alternatively, for direct introduction thereof via a gas sampling valve into a gas-liquid chromatograph for analysis. A radiant furnace divided into two compartments, an upper compartment and a lower compartment, was used as a heat source throughout the reaction period. The lower compartment maintained a constant temperature in the reaction zone while the upper compartment maintained a lower, albeit constant, temperature (approximately 450° C.) in the gas expansion zone. The temperature was measured with a thermocouple in a temperature well positioned inside the length of the reactor.

(2) Fixed Bed—A stainless steel tube 20.32 centimeters (8 inches) in length and 0.95 centimeter (0.375 inch) in internal diameter having a usable capacity of 11 milliliters was employed as a fixed bed reactor for the toluene conversion reaction. The reactor was arranged vertically and equipped at the upper end with reactant inlet means having calibrated flow controllers and vaporizers, and at the lower end with reaction effluent outlet means for collecting the reaction effluent or, alternatively, for direct introduction thereof via a gas sampling valve into a gas-liquid chromatograph for analysis. The outlet means was also equipped with means for introducing an inert gas diluent—ntrogen or helium, for example—into the reaction effluent for analysis purposes. A radiant furnace was used to maintain a constant temperature during the reaction period. The temperature was measured with a thermocouple in a temperature well located on the lower outside wall of the reactor.

B. Toluene Conversion—The reaction was conducted in a stoichiometric mode of operation under fluidized conditions unless otherwise noted.

(1) Fluidized Bed—The reactor was charged with approximately 15 milliliters of the attrition resistant metal/oxygen composition prepared as described in Examples 2–43, above. The reactor was placed in the two-compartment radiant furnace and heated to the operating temperatures, usually 575° C. for the reaction zone and 450° C. for the gas expansion zone, which temperatures were maintained throughout the reaction period. The reactor was operated at a pressure of $2.53 \times 10^5$ pascals (2.5 atmospheres, 36.7 psia) in a four-step cycle which comprised (a) passing a stream of air through the attrition resistant metal/oxygen composition for a period of time ranging from 5 seconds to 1 hour, usually 30 minutes (composition oxidation or regeneration); (b) purging the system with a ½ mole ratio feed mixture of nitrogen and water for 1 minute (purge); (c) feeding a toluene/water mixture having a ½ mole ration through the system for 3 minutes (toluene dehydrocoupling or composition reduction); and (d) purging the system as in step (b) (purge). The cycle was then repeated. The total molar feed rate during each step of the four-step cycle was maintained at 15-17 millimoles/minute (about 557 cc/minute) flow rate which, under reaction conditions, provided a linear gas velocity of about 8.23 centimeter/second (0.27 ft/sec) and a superficial reactor residence (contact) time of about 4 seconds unless specified otherwise. Samples of the reaction effluent were taken at 30-second intervals for analysis by gas-liquid chromatography. The results, integrated over the 3-minute reaction period. Steam and toluene in a 2:1 mole ratio were fed to the reactor at a pressure of $2.53 \times 10^5$ pascals (2.5 atmospheres, 36.7 psia) at a rate sufficient to provide a reactor residence (contact) time of 3 seconds (unless otherwise noted) for the toluene (assuming a 50% void space in the reactor). After the reaction had proceeded for 1 minute, the reaction effluent, diluted with helium, was analyzed by gas-liquid chromatography. The results are tabulated in Table 3.

TABLE 3

| METAL/OXYGEN COMPOSITION NO. | TEMPERATURE, °C./-SUPERFICIAL CONTACT TIME, SECONDS[1] | CONVERSION, MOLE % | SELECTIVITY, MOLE % | | |
|---|---|---|---|---|---|
| | | | TRANS-STILBENE | COUPLING[2] | BENZENE |
| 2 | — | — | — | — | — |
| 3 | — | — | — | — | — |
| 4 | — | — | — | — | — |
| 5 | — | — | — | — | — |
| 6 | — | — | — | — | — |
| 7 | — | — | — | — | — |
| 8 | 560/2 | 11.0 | 52.0 | 82.0 | 13.0 |
| 9 | 565/2.4 | 13.0 | 51.0 | 81.0 | 15.0 |
| 10 | — | — | — | — | — |
| 11 | — | — | — | — | — |
| 12 | — | — | — | — | — |
| 13 | — | — | — | — | — |
| 14 | — | — | — | — | — |
| 15 | — | — | — | — | — |
| 16 | 520/2 | 8.0 | 56.0 | 74.0 | 16.0 |
| 17 | 535/2 | 9.0 | 61.0 | 73.0 | 17.0 |
| 18 | 550/2 | 19.0 | 69.0 | 83.0 | 14.0 |
| 19 | — | — | — | — | — |
| 20 | 560 | 41.0 | 74.0 | 79.0 | 11.0 |
| 21 | 560 | 17.0 | 53.0 | 83.0 | 8.0 |
| 22 | 560 | 10.0 | 43.0 | 62.0 | 21.0 |
| 23 | 560 | 39.0 | 68.0 | 71.0 | 17.0 |
| 24 | 560 | 44.0 | 74.0 | 75.0 | 14.0 |
| 25 | 560 | 42.0 | 72.0 | 75.0 | 14.0 |
| 26 | 560 | 41.0 | 74.0 | 78.0 | 11.0 |
| 27 | 575 | 17.0 | 70.0 | 82.0 | 10.0 |
| 28 | 560 | 25.0 | 68.0 | 78.0 | 12.0 |
| 29 | 540 | 26.0 | 62.0 | 77.0 | 10.0 |
| 30 | 570 | 35.0 | 62.0 | 67.0 | 14.0 |
| 31 | 565 | 44.0 | 63.0 | 67.0 | 18.0 |
| 32 | 560 | 32.0 | 65.0 | 71.0 | 17.0 |
| 33 | 560 | 33.0 | 69.0 | 73.0 | 16.0 |
| 34 | 560 | 48.0 | 75.0 | 79.0 | 12.0 |
| 35 | 560 | 36.0 | 77.0 | 82.0 | 9.0 |
| 36 | 560 | 37.0 | 77.0 | 85.0 | 8.0 |
| 37-A | 575/ | 11.0 | 47.7 | 81.2 | 11.9 |
| | 560/7.4 | 38.0 | 62.0 | 79.1 | 12.6 |
| 37-B | 535/0.6 | 5.2 | 48.2 | 87.2 | 5.6 |
| 37-C | 570/0.6 | 6.7 | 45.8 | 79.6 | 8.1 |
| 37-D | 565/0.6 | 7.7 | 50.4 | 79.4 | 11.9 |
| 37-E | 590/1.2 | 7.6 | 34.6 | 78.6 | 15.5 |
| 37-F | 575/1.2 | 13.5 | 53.9 | 87.1 | 7.9 |
| 38-A | 575/1.5 | 30.0 | 50.0 | 76.7 | 13.0 |
| 38-B | 540 | 30.0 | 62.0 | 83.0 | 10.0 |
| 38-C | 570/2 | 36.0 | 58.0 | 77.1 | 13.0 |
| 39 | 565/2 | 40.0 | 62.0 | 76.0 | 16.0 |
| 40 | 540/2 | 23.0 | 70.0 | 79.0 | 16.0 |
| 41 | 550/2.5 | 26.0 | 57.0 | 67.0 | 18.0 |
| 42[3] | 580/3 | 22.0 | 61.0 | 82.0 | 18.0 |
| 43[3] | 580/3 | 25.0 | 59.0 | 77.0 | 21.0 |

[1]A superficial contact time of about 4 seconds was employed in the fluidized bed toluene conversion runs unless specified otherwise.
[2]Selectivity to trans-stilbene + (cis stilbene + bibenzyl).
[3]Fixed bed reactor was employed.

dehydrocoupling step (c) period, are tabulated in Table 3.

(2) Fixed Bed—The reactor was charged with approximately 11 milliliters of the attrition resistant metal/oxygen composition prepared as described in Examples 2–43, above. Glass wool plugs were used as supports for the composition. The charged reactor was placed in a radiant furnace and heated to maintain a constant temperature throughout the

EXAMPLE 46

This procedure illustrates a method of separating the stilbene in pure form.

Collect product streams from a number of toluene dehydrocoupling reactions in dry ice chilled traps. Flash distill the combined streams to a 200° C. bottoms temperature and then batch distill through a 2.5-centimeter inside diameter×90.0-centimeter long column packed with extruded metal. Collect the fraction having a boiling point at about 186° C./20 mm mercury as transtilbene. The stilbene product is a white, crystalline solid having a melting point of 124°–125° C. and a retention time identical with an authentic sample of transstilbene as determined by gas chromatographic coinjection.

Molten trans-stilbene reacts rapidly with atmospheric oxygen to form numerous oxygenated (or polar) impurities, a major constituent of which is benzophenone. As a result, molten trans-stilbene should be protected from exposure to the atmosphere. Trans-stilbene so contaminated can be purified by recrystallization from 95% ethanol to yield pure product.

Thus, it is apparent that there has been provided, in accordance with the present invention, attrition resistant metal/oxygen compositions, a process for preparing same, and a process for utilizing such compositions to transform organic compounds, for example, to dehydrocouple toluene to yield toluene dehydrocoupled products, that fully satisfy the objects and advantages set forth hereinabove. While the invention has been described with respect to various specific examples and embodiments thereof, it is understood that the invention is not limited thereto and that many alternatives, modifications, and variations will be apparent to those skilled in the art in light of the foregoing description. Accordingly, it is intended to embrace all such alternatives, modifications, and variations as fall within the spirit and broad scope of the invention.

What is claimed is:

1. An attrition resistant metal/oxygen composition which comprises the infusion and reaction product of:
   (a) 35 to 80 mole percent of an alumina existing in a crystal form selected from the group consisting of $\gamma$, $\delta$, $\eta$, and $\chi$ crystal forms, and mixtures thereof, or that can be transformed by heat to such crystal forms, and characterized by
      (i) a mean particle size from about 10 $\mu$m to about 200 $\mu$m,
      (ii) a fractional porosity of at least 0.2,
      (iii) a surface area of at least 150 m²/g, and
      (iv) a pore diameter such that at least 10 percent of the pores are less than 55 Å, and
   (b) 20 to 65 mole percent of at least one metal oxide, or compound convertible by heat to such metal oxide, having a maximum mean particle size of about 100 $\mu$m, with the proviso that the alumina/metal oxide mean particle size ratio is at least 2, which metal oxide is susceptible of undergoing infusion and reaction with the alumina upon being subjected to temperatures of at least 0.4 $T_m$ for a time sufficient to cause infusion and reaction between the metal oxide and the alumina, wherein $T_m$ is the melting point in °K. of the alumina wherein the composition is represented by the empirical formula selected from the group consisting of $Pb_{10}Sb_3Bi_2O_x(Al_2O_3)_{7-28}$, $Bi_{15-30}K_{4-5}Zr_{1-2}O_x(Al_2O_3)_{16-29}$, $(PbO_x)_3(Al_2O_3)_4$, $Pb_5BiO_x(Al_2O_3)_{18}$, $Pb_{10}Sb_3Bi_2KO_x(Al_2O_3)_{19}$, $Bi_{15}Ca_5ZrO_x(Al_2O_3)_{16}$, $Bi_5Fe_5Ca_5BO_x(Al_2O_3)_8$, and $Bi_2Fe_2Ca_2O_x(Al_2O_3)_3$.

2. The composition of claim 1 wherein the mean particle size of the alumina is from about 20 $\mu$m to about 125 $\mu$m.

3. The composition of claim 1 wherein the alumina has a fractional porosity from about 0.2 to about 0.8.

4. The composition of claim 1 wherein the alumina particles are spheroidal.

5. The composition of claim 1 wherein the alumina is a hydrated alumina selected from the group consisting of Boehmite, pseudo-Boehmite, Bayerite, and Gibbsite.

6. The composition of claim 1 wherein the alumina/metal oxide mean particle size ratio is 15 or more.

7. The composition of claim 1 wherein the metal oxide component concentration is in an amount from about 30 mole percent to about 55 mole percent.

8. The composition of claim 1 wherein the composition is represented by the empirical formula $$Pb_{10}Sb_3Bi_2O_x(Al_2O_3)_{7-28}$$

wherein x is a number taken to satisfy the average valences of Pb, Sb, and Bi in the oxidation states in which they exist in the composition.

9. The composition of claim 1 wherein the composition is represented by the empirical formula $$(PbO_x)_3(Al_2O_3)_4$$

wherein x is a number taken to satisfy the average valence of Pb in the oxidation state in which it exists in the composition.

10. The composition of claim 1 wherein the composition is represented by the empirical formula $$Pb_5BiO_x(Al_2O_3)_{18}$$

wherein x is a number taken to satisfy the average valence of Pb and Bi in the oxidation state in which they exist in the composition.

11. The composition of claim 1 wherein the composition is represented by the empirical formula $$Pb_{10}Sb_3Bi_2KO_x(Al_2O_3)_{19}$$

wherein x is a number taken to satisfy the average valences of Pb, Sb, Bi, and K in the oxidation states in which they exist in the composition.

12. The composition of claim 1 wherein the composition is represented by the empirical formula $$Bi_{15-30}K_{4-5}Zr_{1-2}O_x(Al_2O_3)_{16-29}$$

wherein x is a number taken to satisfy the average valences of Bi, K, and Zr in the oxidation states in which they exist in the composition.

13. The composition of claim 1 wherein the composition is represented by the empirical formula $$Bi_{15}Ca_5ZrO_x(Al_2O_3)_{16}$$

wherein x is a number taken to satisfy the average valences of Bi, Ca, and Zr in the oxidation states in which they exist in the composition.

14. The composition of claim 1 wherein the composition is represented by the empirical formula $$Bi_5Fe_5Ca_5BO_x(Al_2O_3)_8$$

wherein x is a number taken to satisfy the average valences of Bi, Fe, Ca, and B in the oxidation states in which they exist in the composition.

15. The composition of claim 1 wherein the composition is represented by the empirical formula $Bi_2Fe_2Ca_2O_x(Al_2O_3)_3$ wherein x is a number taken to satisfy the average valences of Bi, Fe, and Ca in the oxidation states in which they exist in the composition.

16. The composition of claim 1 wherein the composition exhibits an attrition rate less than 0.5 weight percent/hour.

17. The composition of claim 1 wherein the composition exhibits a surface area less than 5 m²/g.

18. A process for the preparation of an attrition resistant metal/oxygen composition which comprises:
   (a) forming a mixture of 35 to 80 mole percent of an alumina existing in a crystal form selected from the group consisting of γ, δ, η, and χ crystal forms, and mixtures thereof, or that can be transformed by heat to such crystal forms, and characterized by
      (i) a mean particle size from about 10 μm to about 200 μm,
      (ii) a fractional porosity of at least 0.2,
      (iii) a surface area of at least 150 m²/g, and
      (iv) a pore diameter such that at least 10 percent of the pores are less than 55 Å,
   and 20 to 65 mole percent of at least one metal oxide, or compound convertible by heat to such metal oxide, having a maximum mean particle size of about 100 μm, with the proviso that the alumina/metal oxide mean particle size ratio is at least 2, which metal oxide is susceptible of undergoing infusion and reaction with the alumina and
   (b) heating the mixture to a temperature of at least 0.4 $T_m$ for a time sufficient to cause infusion and reaction between the metal oxide and the alumina, wherein $T_m$ is the melting point in °K of the alumina, and
   (c) recovering a composition represented by the empirical formula selected from the group consisting of $Pb_{10}Sb_3Bi_2O_x(Al_2O_3)_{7-28}$, $Bi_{15-30}K_{4-5}Zr_{1-2}O_x(Al_2O_3)_{16-29}$, $(PbO_x)_3(Al_2O_3)_4$, $Pb_5BiO_x(Al_2O_3)_{18}$, $Pb_{10}Sb_3Bi_2KO_x(Al_2O_3)_{19}$, $Bi_{15}Ca_5ZrO_x(Al_2O_3)_{16}$, $Bi_5Fe_5Ca_5BO_x(Al_2O_3)_8$, and $Bi_2Fe_2Ca_2O_x(Al_2O_3)_3$.

19. The process of claim 18 wherein the mean particle size of the alumina is from about 20 μm to about 125 μm.

20. The process of claim 18 wherein the alumina has a fractional porosity from about 0.2 to about 0.8.

21. The process of claim 18 wherein the alumina particles are spheroidal.

22. The process of claim 18 wherein the alumina is a hydrated alumina selected from the group consisting of Boehmite, pseudo-Boehmite, Bayerite, and Gibbsite.

23. The process of claim 18 wherein the alumina/metal oxide mean particle size ratio is 15 or more.

24. The process of claim 18 wherein the metal oxide component concentration is in an amount from about 30 mole percent to about 55 mole percent.

25. The process of claim 18 wherein the composition is represented by the empirical formula $Pb_{10}Sb_3Bi_2O_x(Al_2O_3)_{7-28}$ wherein x is a number taken to satisfy the average valences of Pb, Sb, and Bi in the oxidation states in which they exist in the composition.

26. The process of claim 18 wherein the composition is represented by the empirical formula $(PbO_x)_3(Al_2O_3)_4$ wherein x is a number taken to satisfy the average valence of Pb in the oxidation state in which it exists in the composition.

27. The process of claim 18 wherein the composition is represented by the empirical formula $Pb_5BiO_x(Al_2O_3)_{18}$ wherein x is a number taken to satisfy the average valences of Pb and Bi in the oxidation states in which they exist in the composition.

28. The process of claim 18 wherein the composition is represented by the empirical formula $Pb_{10}Sb_3Bi_2KO_x(Al_2O_3)_{19}$ wherein x is a number taken to satisfy the average valences of Pb, Sb, Bi, and K in the oxidation states in which they exist in the composition.

29. The process of claim 18 wherein the composition is represented by the empirical formula $Bi_{15-30}K_{4-5}Zr_{1-2}O_x(Al_2O_3)_{16-29}$ wherein x is a number taken to satisfy the average valences of Bi, K, and Zr in the oxidation states in which they exist in the composition.

30. The process of claim 18 wherein the composition is represented by the empirical formula $Bi_{15}Ca_5ZrO_x(Al_2O_3)_{16}$ wherein x is a number taken to satisfy the average valences of Bi, Ca, and Zr in the oxidation states in which they exist in the composition.

31. The process of claim 18 wherein the composition is represented by the empirical formula $Bi_5Fe_5Ca_5BO_x(Al_2O_3)_8$ wherein x is a number taken to satisfy the average valences of Bi, Fe, Ca, and B in the oxidation states in which they exist in the composition.

32. The process of claim 18 wherein the composition is represented by the empirical formula $Bi_2Fe_2Ca_2O_x(Al_2O_3)_3$ wherein x is a number taken to satisfy the average valences of Bi, Fe, and Ca in the oxidation states in which they exist in the composition.

33. The process of claim 18 wherein the alumina and the metal oxide are dry mixed.

34. The process of claim 18 wherein the alumina and the metal oxide are mixed by slurrying in a suitable wetting agent.

35. The process of claim 34 wherein the wetting agent is water.

36. The process of claim 34 wherein the wetting agent is an organic compound selected from the group consisting of methanol and ethanol.

37. The process of claim 34 wherein the wetting agent is removed from the slurried mixture of alumina and metal oxide by heating the mixture at a temperature of about 150° C. to about 250° C. for about 1 hour to about 5 hours.

38. The process of claim 18 wherein the mixture of alumina and metal oxide is heated to a temperature from about 0.47 $T_m$ to about 0.74 $T_m$ for a time from about 1 hour to about 15 hours.

39. The process of claim 38 wherein 0.47 $T_m$ is about 800° C. and 0.74 $T_m$ is about 1400° C.

40. The process of claim 18 wherein the composition exhibits an attrition rate less than 0.5 weight percent/hour.

41. The process of claim 18 wherein the composition exhibits a surface area less than 5 $m^2/g$.

* * * * *